US008586775B2

(12) United States Patent
Gribble et al.

(10) Patent No.: US 8,586,775 B2
(45) Date of Patent: *Nov. 19, 2013

(54) THERAPEUTIC COMPOUNDS AND METHODS OF USE

(75) Inventors: Gordon W. Gribble, Norwich, VT (US); Tadashi Honda, Hanover, NH (US); Michael B. Sporn, Tunbridge, VT (US); Nanjoo Suh, Hanover, NH (US)

(73) Assignee: Trustees of Dartmouth College, Hanover, NH (US)

(*) Notice: Subject to any disclaimer, the term of this patent is extended or adjusted under 35 U.S.C. 154(b) by 45 days.

This patent is subject to a terminal disclaimer.

(21) Appl. No.: 13/217,127

(22) Filed: Aug. 24, 2011

(65) Prior Publication Data
US 2013/0237721 A1 Sep. 12, 2013

Related U.S. Application Data

(60) Continuation of application No. 11/927,418, filed on Oct. 29, 2007, now Pat. No. 8,034,955, which is a continuation of application No. 10/395,372, filed on Mar. 24, 2003, now Pat. No. 7,288,568, which is a continuation of application No. 09/927,081, filed on Aug. 9, 2001, now Pat. No. 6,552,075, which is a division of application No. 09/335,003, filed on Jun. 17, 1999, now Pat. No. 6,326,507.

(60) Provisional application No. 60/090,053, filed on Jun. 19, 1998.

(51) Int. Cl.
C07C 255/49 (2006.01)

(52) U.S. Cl.
USPC ........................................... 558/415

(58) Field of Classification Search
USPC ........................................... 558/415
See application file for complete search history.

(56) References Cited

U.S. PATENT DOCUMENTS

| | | | |
|---|---|---|---|
| 4,395,423 A | 7/1983 | Neumann | 424/304 |
| 4,808,614 A | 2/1989 | Hertel | 514/45 |
| 5,013,649 A | 5/1991 | Wang et al. | 435/69.1 |
| 5,064,823 A | 11/1991 | Lee et al. | 514/198 |
| 5,401,838 A | 3/1995 | Chou | 536/281 |
| 5,426,183 A | 6/1995 | Kjell | 536/285.5 |
| 5,464,826 A | 11/1995 | Grindey et al. | 514/50 |
| 5,521,294 A | 5/1996 | Wildfeuer | 536/187 |
| 5,597,124 A | 1/1997 | Kessel et al. | 241/30 |
| 5,603,958 A | 2/1997 | Morein et al. | 424/489 |
| 5,606,048 A | 2/1997 | Chou et al. | 536/271.1 |
| 5,972,703 A | 10/1999 | Long et al. | 435/372 |
| 6,025,395 A | 2/2000 | Breitner et al. | 514/570 |
| 6,303,569 B1 | 10/2001 | Greenwald et al. | 514/2 |
| 6,326,507 B1 | 12/2001 | Gribble et al. | 558/415 |
| 6,485,756 B1 | 11/2002 | Aust et al. | 424/725 |
| 6,552,075 B2 | 4/2003 | Gribble et al. | 514/522 |
| 6,974,801 B2 | 12/2005 | Honda et al. | 514/25 |
| 7,176,237 B2 | 2/2007 | Honda et al. | 514/519 |
| 7,265,096 B2 | 9/2007 | Gallop et al. | 514/49 |
| 7,288,568 B2 | 10/2007 | Gribble et al. | 514/519 |
| 7,435,755 B2 | 10/2008 | Konopleva et al. | 514/510 |
| 8,034,955 B2 * | 10/2011 | Gribble et al. | 548/241 |
| 2002/0042535 A1 | 4/2002 | Gribble et al. | 558/429 |
| 2005/0276836 A1 | 12/2005 | Wilson et al. | 424/434 |
| 2005/0288363 A1 | 12/2005 | Gribble et al. | 558/303 |
| 2007/0155742 A1 | 7/2007 | Honda et al. | 514/519 |
| 2008/0220057 A1 | 9/2008 | Gribble et al. | 514/522 |
| 2009/0048204 A1 | 2/2009 | Walling et al. | 514/49 |
| 2009/0060873 A1 | 3/2009 | Sporn et al. | 424/85.6 |
| 2009/0093447 A1 | 4/2009 | Konopleva et al. | 514/510 |

FOREIGN PATENT DOCUMENTS

| | | |
|---|---|---|
| DE | 10 2005 04161 | 3/2007 |
| EP | 0 272 891 A2 | 6/1988 |
| EP | 0 329 348 B1 | 7/1995 |
| EP | 0 376 518 B1 | 11/1995 |
| EP | 0 576 230 B1 | 4/1996 |
| EP | 0 577 303 B1 | 10/1997 |
| EP | 0 712 860 B1 | 12/2001 |
| JP | 55-55153 | 4/1980 |
| WO | WO 91/15498 | 10/1991 |
| WO | WO 98/00173 | 1/1998 |
| WO | WO 98/32762 | 7/1998 |
| WO | WO 99/33483 | 7/1999 |
| WO | WO 99/65478 | 12/1999 |
| WO | WO 00/73253 | 12/2000 |
| WO | WO 01/01135 | 1/2001 |
| WO | WO 02/03996 | 1/2002 |
| WO | WO 02/047611 | 6/2002 |
| WO | WO 03/043631 | 5/2003 |
| WO | WO 03/059339 | 7/2003 |
| WO | WO 2005/042002 | 5/2005 |
| WO | WO 2005/046732 | 5/2005 |
| WO | WO 2006/029221 | 3/2006 |
| WO | WO 2007/005879 | 1/2007 |
| WO | WO 2007/069895 | 6/2007 |
| WO | WO 2008/111497 | 9/2008 |
| WO | WO 2008/136838 | 11/2008 |
| WO | WO 2009/023232 | 2/2009 |

OTHER PUBLICATIONS

Couch et al., Studies on the reactivity of CDDO, a promising new chemo preventive and chemotherapeutic agent: implications for a molecular mechanism of action; Bioorganic and Medicinal Chemistry Letters (2005), 15(9), 2215-2219.*
Agarwal and Mehta, "Possible involvement of Bc1-2 pathway in retinoid X receptor alpha-induced apoptosis of HL-60 cells," *Biochem Biophys Res Commun*, 230(2):251-253, 1997.
Baeuerle, "The NF-κB: ten years after," *Cell*, 87:13-20, 1996.
Baldwin, Jr., "The NF-κB and IκB proteins: new discoveries and insights," *Annu. Rev. Immunol.*, 14:649-681, 1996.

(Continued)

Primary Examiner — James O Wilson
Assistant Examiner — Ebenezer O Sackey
(74) Attorney, Agent, or Firm — Parker Highlander PLLC

(57) ABSTRACT

Compounds and methods useful for chemopreventative treatment of diseases such as cancer, Alzheimer's disease, Parkinson's disease, inflammatory bowel diseases, and multiple sclerosis.

1 Claim, 11 Drawing Sheets

(56) References Cited

OTHER PUBLICATIONS

Barkett and Gilmore, "Control of apoptosis by Rel/NF-κB transcription factors," *Oncogene*, 18:6910-6924, 1999.

Barnes and Karin, "Nuclear factor-κB—a pivotal transcription factor in chronic inflammation diseases," *N. Engl. J. Med.*, 336:1066-1071, 1997.

Begum et al., "Synthesis of 2β-hydroxyursolic acid and other ursane analogs from ursonic acid," *Australian Journal of Chemistry*, 46 (7): 1067-1071, 1993.

Beran et al., "Topotecan and cytarabine is an active combination regimen in myelodysplastic syndromes and chronic myelomonocytic leukemia," *J Clinical Oncology*, 17(9):2819-2830, 1999.

Bliard et al., "Glycosylation of acids under phase transfer conditions. Partial synthesis of saponins," *Tetrahedron Lett.*, 35:6107-6108, 1994.

Bollag and Holdener, "Retinoids in cancer prevention and therapy," *Annals of Oncology*, 3:513-526, 1992.

Bore et al., "The anti-inflammatory triterpenoid methyl 2-cyano-3, 12-dioxoolean 1,9(11)-dien-28-oate methanol solvate hydrate," Acta Crystallorg C., 58(Pt 3):o199-o200, 2002.

Bowden et al., "Constituents of the fruit of *Pseudopanax arboreum* (Araliaceae)," *Australian J. of Chemistry*, 28 (1): 91-107, 1975.

Cai and Vasella, "A new protecting group for alkynes: orthogonally protected dialkynes," *Helv. Chim. Acta.*, 78:732-757, 1995.

Campbell et al., "Endocyclic a,β-unsaturated ketones. VI. Ultraviolet and infrared absorption spectra and resonance stabilization," *Bioorganic and Medicinal Chemistry Letters*, 7(13): 1623-1628, 1997.

Carter et al., "Expression of survivin, a member of the inhibitor of apoptosis (IAP) family of caspase inhibitors is expressed in AML and regulated by cytokines and ATRA," *Blood*, 94(Suppl 1):479a, Abstract # 2142, 1999.

Cassady and Suffness, In *Anticancer Agents Based on Natural Product Models*; Academic Press, NY, 254-269, 1980.

Castaigne et al., "All-trans retinoic acid as a differentiation therapy for acute promyelocytic leukemia," *Blood*, 76(9):1704-1709, 1990.

Chattopadhyay et al., "Studies on autoxidation: Part IV. Synthesis of isomeric 2,3-diols of olean-12-en-28-oate and isohopane (moretane)," *Indian J. of Chemistry, Section B: Organic Chemistry Including Medicinal Chemistry*, 15 (1): 21-24, 1977.

Chou et al., "Sterospecific Synthesis of 2-Deoxy-2, 2-difluororibonolactone and its Use in the Preparation of 2'-Deoxy-2', 2'-difluoro-B—D-ribofuranosyl Pyrimidine Nucleosides: The Key Role of Selective Crystallization," *Synthesis*, 565-570, 1992.

Chung and Wasicak, "Synthesis of chiral ∀-acetylenic cyclic amines from ∀-amino acids: App.s to differentially constrained oxotremorine analogues as muscarinic agents," *Tetrahedron Lett.*, 31:3957-3960, 1990.

Clinton et al., "Steroidal[3,2-c]pyrazoles. II. Androstanes, 19-norandrostanes and their unsaturated analogs," *J Am Chem Soc.*, 83:1478-1491, 1961.

Corey and Ruden, "Stereoselective methods for the synthesis of terminal *cis* and *trans*enyne units," *Tetrahedron Lett.*, 1495-1499, 1973.

Cripe, "Adult Acute Leukemia," *Current Problems in Cancer*, 21 (1): 4-64, 1997.

Dean et al., "Halogenolysis of methyl glycyrrhetate with lithium iodidedimethylformamide," *J. Chem. Soc.*, 6655-6659, 1965.

Devi et al., "Constituents of black dammar resin and some transformation products of α- and and β-amyrins," *Indian J. Of Chemistry*, 7 (12): 1279-1280, 1969.

Ding et al., "Macrophage deactivating factor and transforming growth factors-beta 1, beta2, and beta3 inhibit induction of macrophage nitrogen oxide synthesis by IFN-gamma," *J. Immunol.*, 940-944, 1990.

Drach et al., "Induction of differentiation in myeloid leukemia cell lines and acute promyelocytic leukemia cells by liposomal all-trans-retinoic acid," Cancer Research, 53:2100-2104, 1993.

Dragnev et al., "The retinoids and cancer prevention mechanisms," *The Oncologist*, 5:361-368, 2000.

Drefahl and Huneck, "Nor-olea-12-enol-17-amin and Olea-12-enol-28-amin," *Chem. Ber.*, 91:278-281, 1958.

DuBois et al., "$G_1$ delay in cells overexpressing prostaglandin endoperoxide synthase-$2^1$," *Cancer Res.*, 56(4):733-737, 1996.

DuBois et al., "Increased cyclooxygenase-2 levels in carcinogen-induced rat colonic tumors," *Gastroenterology*, 110:1259-1262, 1996.

Dutcher et al., "Pentacyclic triterpene synthesis. 5. Synthesis of optically pure ring AB precursors," *J. Org. Chem.*, 41:2663-2669, 1976.

Elgamal et al., "Glycyrrhetic acid derivatives with modified ring A," *J of Pharmaceutical Sciences*, 62 (9): 1557-1558, 1973.

Elgamal et al., "The C-2,C-3-glycol derivatives of glycyrrhetic acid," *Tetrahedron*, 30 (23/24): 4083-4087, 1974.

Elstner et al., "Ligands for peroxisome proliferator-activated receptorgamma and retinoic acid receptor inhibit growth and induce apoptosis of human breast cancer cells in vitro and in BNX mice," *Proc. Natl. Acad. Sci. USA*, 95:8806-8811, 1998.

Embleton et al., "Antitumour reactions of monoclonal antibody against a human osteogenic-sarcoma cell line," *Br. J. Cancer*, 43:4801-4805, 1981.

Endová et al., "Preparation of 2,3-secodiacids of the lupane series," *Collection of Czechoslovak Chemical Communications*, 59 (6): 1420-1429, 1994.

Engel et al., "Quantitation of minimal residual disease in acute myelogenous leukemia and myelodysplastic syndromes in complete remission by molecular cytogenetics of progenitor cells," *Leukemia*, 13:568-577, 1999.

Estey et al., "Molecular remissions induced by liposomal-encapsulated all-trans retinoic acid in newly diagnosed acute promyelocytic leukemia," *Blood*, 94:2230-2235, 1999.

Estey et al., "Randomized phase II study of fludarabine + cytosine arabinoside + idarubicin + all-trans retinoic acid + granulocyte-colony stimulating factor in poor prognosis newly diagnosed acute myeloid leukemia and myelodysplastic syndrom," *Blood*, 93(8):2478-2484, 1999.

Evers et al., "Betulinic acid derivatives: a new class of human immunodeficiency virus type 1 specific inhibitors with a new mode of action," *J of Medicinal Chemistry*, 39 (5): 1056-1068, 1996.

Finkbeiner and Stiles, "Chelation as a driving force in organic reactions. IV. Synthesis of a ∀-nitro acids by control of the carboxylastion-decarboxylation equilibrum," *J. Am. Chem. Soc.*, 85:616-622, 1963.

Finlay et al., "The effects of A and C ring modification of oleanolic and ursolic acid on the inhibition of nitric oxide formation in mouse macrophages," 213th ACS National Meeting, San Francisco, California, abstract, Apr., 13-17, 1997.

Finlay et al., "The effects of A and C ring modification of oleanolic and ursolic acid on the inhibition of nitric oxide formation in mouse macrophages," 213th ACS National Meeting, San Francisco, California, poster, Apr., 13-17, 1997.

Ganguly et al., "Oxidation of ring in a lupeol," *Tetrahedron*, 22 (10): 3597-3599, 1966.

García-Granados et al., "Semi-synthesis of triterpene A-ring derivatives from oleanolic and maslinic acids. Part II. Theoretical and experimental $^{13}C$ chemical shifts," *J. of Chemical Research*, Synopses, 2: 56-57, 2000.

García-Granados et al., "Semi-synthesis of triterpene A-ring derivatives from oleanolic and maslinic acids. Part II. Theoretical and experimental $^{13}C$ chemical shifts," *J. Of Chemical Research*, Synopses, 5: 211-212, 2000.

Genain and Hauser, "Creation of a model for multiple sclerosis in *Callithrix jacchus* marmosets," *J. Mol. Med.*, 75:187-197, 1997.

Ghosh et al., "NF-κB and Rel proteins: evolutionarily conserved mediators of immune response," *Annu Rev Immunol.*, 16:225-260, 1998.

Glen et al., "Isolation of a new triterpenoid from rose-bay willow-herb," *Chemistry and Industry*, London, United Kingdom), 46: 1908, 1965.

Govindachari et al., "Gymnosporol, a new pentacyclic triterpene from *Gymnosporia rothiana*," Indian Journal of Chemistry, 8 (5): 395-397, 1970.

(56) References Cited

OTHER PUBLICATIONS

Green and Long, "Compounds related to the steroid hormones. Part II. The action of hydrogen bromide on 2-bromo-3-oxo-$\Delta^1$-5α-steroids," *J. of the Chemical Society*, 2532-2543, 1961.
Grieco and Speake, "Synthetic Studies on Quassinoids: Total Synthesis and Biological Evaluation of (+)-Des-D-chaparrinone," *J. Org. Chem.*, 63:5929-5936, 1998.
Guo et al., "Selective Protection of 2',2'-Diflurodeoxycytidine (Gemcitabine)," *J. Org. Chem.*, 64: 8319-8322, 1999.
Gura et al., "Systems for identifying new drugs are often faulty," *Science*, 278:1041-1042, 1997.
Guttridge et al., "NF-kappaB controls cell growth and differentiation through transcriptional regulation of cyclin D1," *Mol. Cell. Biol.*, 19 (8): 5785-5799, 1999.
Hanna and Ourisson, "Studies of cyclic ketones. VIII. Preparation and properties of polycyclic α-diketones," *Bulletin de la Societe Chimique de France*, 1945-1951, 1961. (French only, but see attached English CAPLUS database summary.).
Hattori et al., "A triterpene from the fruits of *Rubus chingii*," *Phytochemistry*, 27 (12): 3975-3976, 1988.
Heiner et al., "Localization of GD2-specific monoclonal antibody 3F8 in human osteosarcoma," *Cancer Res.*, 47:5377-5384, 1987.
Hinz et al., "NF-kappaB function in growth control: regulation of cyclin D1 expression and G0/G1-to-S-phase transition," *Mol. Cell. Biol.*, 19 (4): 2690-2698, 1999.
Hirota et al., "Stereoselective total synthesis of (±)-eperuane-8β,15-diol[1]," *Bull. Chem. Soc. Jpn.*, 61:4023-4028, 1988.
Hirota et al., "Total synthesis of (±)-amarolide, a quassinoid bitter principle," *J. Org. Chem.*, 56:1119-1127, 1991.
Hirota et al.,"Suppression of tumor promoter-induced inflammation of mouse ear by ursolic acid and 4,4-dimethycholestane derivatives"*Agric. Biol. Chem.*, 54:1073-1075, 1990.
Honda et al., "Design and synthesis of 2-cyano-3,12-dioxoolean-1,9-dien-28-oic acid, a novel and highly active inhibitor of nitric oxide production in mouse macrophages," *Bioorg Med Chem Lett.*, 8(19):2711-2714, 1998.
Honda et al., "New enone derivatives of oleanolic acid and ursolic acid as inhibitors of nitric oxide production in mouse macrophages," *Bioorg. Med. Chem. Lett.*, 7:1623-1628, 1997.
Honda et al., "New synthetic oleanane and ursane triterpenoids as inhibitors of nitric oxide production in mouse macrophages," 5th Chemical Congress of North America Meeting, Cancun, Mexico, abstract, Nov. 11-15, 1997.
Honda et al., "New synthetic oleanane and ursane triterpenoids as inhibitors of nitric oxide production in mouse macrophages," 5th Chemical Congress of North America Meeting, Cancun, Mexico, slides from oral presentation and poster, Nov. 11-15, 1997.
Honda et al., "Novel synthetic oleanane and ursane triterpenoids with various enone functionalities in ring a as inhibitors of nitric oxide production in mouse macrophages," *J. Med. Chem.*, 43:1866-1877, 2000.
Honda et al., "Novel synthetic oleanane triterpenoids: a series of highly active inhibitors of nitric oxide production in mouse macrophages," *Bioorg Med Chem Lett*, 9(24):3429-3434, 1999.
Honda et al., "Synthesis of (±)-3,3-ethylenedioxy-14α-hydroxy-5-picrasene-11,16-dione, a 14αH-picrasane derivative," *Chem. Lett.*, 299-302, 1981.
Honda et al., "Synthetic oleanane and ursane triterpenoids with modified rings A and C: a series of highly active inhibitors of nitric oxide production in mouse macrophages," *J. Med. Chem.*, 43:4233-4246, 2000.
Huang et al., "Inhibition of skin tumorigenesis by Rosemary and its constituents carnosol and ursolic acid," Cancer Res., 54:701-708, 1994.
Huang et al., "Inhibitory effects of dietary curcumin on forestomach, duodenal, and colon carcinogenesis in mice," *Cancer. Res.*, 54:5841-5847, 1994.
Huang et al., "Structure of a WW domain containing fragment of dystrophin in complex with β-dystroglycan, " *Nat. Struct. Biol.*, 7:634-638, 2000.

Huneck, "Triterpene, XIV: die bromierung von 19β28-epoxy-3-oxo-2-diazo- und -1-oxo-2-diazo- sowie von 19β28-epoxy-1-oxo-18α*H*-oleanan," *Chemische Berichte*, 98 (9): 2837-2843, 1965. (German only, but see attached English CAPLUS database summary.).
Iguchi et al., "Lipid peroxidation and disintegration of the cell membrane structure in cultures of rat lung fibroblasts treated with asbestos," *J. Appl. Toxicol.*, 13:269-275, 1993.
Ito et al., "The novel triterpenoid 2-cyano-3, 12-dioxoolean-1,9-dien-28-oic acid induces apoptosis of human myeloid leukemia cells by a caspase-8-dependent mechanism," *Cell Growth & Differentiation*, 11(5):261-267, 2000.
Johnson et al., "A plan for distinguishing between some five- and six-membered ring ketones," *J. Am Chem. Soc.*, 67:1745-1754, 1945.
Joyce et al., "Integration of Rac-dependent regulation of cyclin D1 transcription through a nuclear factor-kappaB-dependent pathway," *J. Biol. Chem.*, 274 (236): 25245-25249, 1999.
Kahne and Collum, "Kinetic cyanations of ketone enolates," *Tetrahedron Lett.*, 22:5011-5014, 1981.
Kaltschmidt et al., "Transcription factor NF-kappaB is activated in primary neurons by amyloid beta peptides and in neurons surrounding early plaques from patients with Alzheimer disease," *Proc. Natl. Acad. Sci. USA*, 94:2642-2647, 1997.
Kawamori et al., "Chemopreventive activity of celecoxib, as specific cyclooxygenase-2 inhibitor, against colon carcinogenesis," *Cancer Res.*, 58(3):409-412, 1998.
Kerwin et al., "Quassinoid synthesis. 2. Preparation of a tetracyclic intermediate having the Bruceantin tetrahydrofuran ring," *J. Org. Chem.*, 52:1686-1695, 1987.
Khan et al., "A dichotomous role for nitric oxide during acute *Toxoplasma gondii* infection in mice," *Proc. Natl. Acad. Sci. USA*, 94:13955-13960, 1997.
Khan et al., "α-amyrin derivatives from *corchorus depressus*," *Phytochemistry*, 30 (6): 1989-1992, 1991.
Kim et al., "Capasase-3 activation is involved in apoptosis induced by a synthetic triterpenoid in Non-small cell lung cancer (NSCLC) cells," *Proc. Amer. Assoc. Cancer Res.*, 41:770, Abstract #4894, 2000.
Kircher, "Triterpenes, in organ pipe cactus," *Phytochemistry*, 19:2707-2712, 1980; Database CAPLUS on STN AN:1981:550946.
Klinot and Vystrcil, "Triterpenes. VII. Stereochemistry of 2-bromo derivatives of allobetuline and alloheterobetaline," *Collection of Czechoslovak Chemical Communications*, 31 (3): 1079-1092, 1966.
Klinot et al., "Triterpenes. Part LXXXVI. Triterpenoid 2,3-ketolis, diols and their acetates: preparation and conformation of the ring A," *Collection of Czechoslovak Chemical Communications*, 54 (2): 400-412, 1989.
Klotz et al., "Selective expression of inducible nitric oxide synthase in human prostate carcinoma," *Cancer*, 82:1897-1903, 1998.
Konopleva and Andreeff, "Regulatory pathways in programmed cell death," *Cancer Mol Biol.*, 6:1229-1260, 1999.
Konopleva et al., "Apoptosis: molecules and mechanisms," *Adv Exp Med Biol*, 457:217-236, 1998.
Konopleva et al., "Engraftment potential of AML progenitors into NOD/scid mice is dependent on baseline CXCR4 expression," *Blood*, 94(Suppl 1):166b, Abstract #3916, 1999.
Konopleva et al., "Novel synthetic triterpenoid CDDO-Me: potent antiproliferative, proapoptotic and differentiating agent in AML," *Blood*, 96(11), Part 1: 121A, abstract # 522, 2000.
Konopleva et al., "Novel synthetic triterpenoid, CDDO, and its methyl ester: Potent antiproliferative, proapoptotic and differentiating agents in AML," *Blood*, 94(Suppl 1):479a, Abstract #2140, 1999.
Konopleva et al., "PPARγ nuclear receptor as a novel therapeutic target in AML," *Blood*, 96(11):460a, Abstract #1982, 2000.
Kornblau et al., "Apoptosis regulating proteins as targets of therapy for hematological malignancies," *Exp. Opin. Inv. Drugs*, 8:2027-2057, 1999.
Kornblau et al., "Phase I study of mitoxantrone plus etoposide with multidrug blockage by SDZ PSC-833 in relapsed or refractory acute myelogenous leukemia," *J. Clin. Oncol.*, 15(5):1796-1802, 1997.
Kowalski and Reddy, "Ester homologation revisited: a reliable, higher yielding and better understood procedure," *J. Org. Chem.*, 57:7194-7208, 1992.

(56) References Cited

OTHER PUBLICATIONS

Kumar and Seshadri, "Triterpenoids of *Pterocarpus santalinus*: constitution of a new lupene diol," *Phytochemistry,* 14 (2): 521-523, 1975.
Kundu et al., "Synthese von 2α-methoxycarbonyl-A-nor-lupa," *Chemische Beerichte,* 101 (9): 3255-3264, 1968. (German only, but see attached English CAPLUS database summary.).
Kurbacher et al., "Ascorbic acid (vitamin C) improves the antineoplastic activity of doxorubicin, cisplatin, and paclitaxel in human breast carcinoma cells in vitro," *Cancer Lett.,* 103:183-189, 1996.
Lala et al., "Role of nitric oxide in tumor progression: lessons from experimental tumors," *Cancer and Metastasis Reviews,* 17 (1): 91-106, 1998.
Langille et al., "Differential effects of physiological concentrations of retinoic acid in vitro on chondrogenesis and myogenesis in chick craniofacial mesenchyme," *Differentiation,* 40:84, 1989.
Lavie and Shvo, "Constituents of *Ecballium elaterium*: proposed structure for elatericin A and B," *Chemistry and Industry,* (London, United Kingdom), 429-430, 1959.
Lawrie et al. "Isolation of derivatives of ursolic acid from apple skin," *Chemistry and Industry,* (London, United Kingdom), 41: 1720, 1966.
Lawson et al., "Isolation and preliminary characterization of a monoclonal antibody that interacts preferentially with the liver isoenzyme of human alkaline phosphatase," *Clin. Chem.,* 31:381-385, 1985.
Lee et al., "Functional and quantitative analysis of splenic T cell immune responses following oral *Toxoplasma gondii* infection in mice, "*Experimental Parasitology,* 91:212-221, 1999.
Lehn and Ourisson, "Nuclear magnetic response (N.M.R.) of natural products. I. General introduction. Triterpenes of the lupane series. Methyl groups," *Bulletin de la Societe Chimique de France,* 1137-1142, 1962. (French only, but see attached English Caplus database summary.).
Lehn and Ourisson, "Syntheses in the lupane series," *Bulletin de la Societe Chimque de France,* 1133-1136, 1962. (French only, but see attached English CAPLUS database summary.).
Lehn and Vystreil, "Resonance magnetique nucleaire de produits naturels—VI : Triterpènes dérivés de la bétuline," *Tetrahedron,* 19 (11): 1733-1745, 1963. (English abstract).
Lemieux, "Acylglycosyl Halides. [55] tetra-O-acetyl-α-D-glucopyranosyl bromide," *Methods Carbohydr. Chem.,* 2:221-222, 1963.
Leonard et al., "Expression of nitric oxide synthase in inflammatory bowel disease is not affected by corticosteroid treatment," *J. Clin. Pathol.,* 51:750-753, 1998.
Lieu et al., "Dual cytotoxic mechanisms of submicromolar taxol on human leukemia HL-60 cells," *Biochem. Pharmacology,* 53:1587-1596, 1997.
Liotta et al., "A simple method for the efficient sysnthesis of unsaturated Ǝ-dicarbonyl compunds," *J. Org. Chem.,* 46:2920-2923, 1981.
Long, "Regulation of human bone marrow-derived osteoprogenitor cells by osteogenic growth factors ," *Clin. Invest.,* 95:881-887, 1995.
Lugemwa et al., "A heliothis zea antifeedant from the abundant birchbark triterpene betulin", *Journal of Agricultural and Food Chemistry,* 38 (2): 493-496, 1990.
MacMicking et al., "Altered responses to bacterial infection and endotoxic shock in mice lacking inducible nitric oxide synthase," *Cell,* 81:641-650, 1995.
Mane and Ingle, "Synthesis and biological activity of some new 1,5-benzothiazepines containing thiazole moiety: 2-aryl-4-(4-methyl -2-substituted-aminothiazol-5-yl)-2,3-dihydro-1, 5-benzothiazepines," *Indian Journal of Chemistry, Section B: Organic Chemistry Including Medicinal Chemistry,* 21B (10): 973-974, 1982.
Manzoor-i-Khuda and Habermehl, "Chemical constituents of *Corchorus capsularis* and *C. olitorium* (jute plant). III. Structure of corosin," *Zeitschrift fuer Naturforschung, Teil C: Biochemie, Biophysik, Biologie, Virologie,*29 (5-6): 209-221, 1974.
Manzoor-i-Khuda, "Isolation techniques for active principles from plants and their composition and structure determination through spectroscopic techniques," *New Trends Nat. Prod.,* 26: 303-323, 1986.
Marnett, "Aspirin and the potential role of prostaglandins in colon cancer," *Cancer Res.,* 52(20):5575-5589, 1992.
Mella et al., "1, 2-dideoxy-3, 4:5, 7-bis-*o* —(1-methylethylidene)— D-gluco- and —D-galacto-hept-1-ynitols : synthesis and conformational studies," *Tetrahedron,* 44:1673-1678, 1988.
Merril and Benveniste, "Cytokines in inflammatory brain lesions: helpful and harmful," *Trends Neurosci.,* 19:331-338, 1996.
Minns et al., "A novel triterpenoid induces transforming growth factor beta production by intraepithelial lymphocytes to prevent ileitis," *Gastroenterology,* 127:119-126, 2004.
Misra et al., "Studies on autoxidation: Part II —synthesis of isomeric 2,3-diols of Δ12- oleanene," *Indian J. Of Chemistry, Section B: Organic Chemistry Including Medicinal Chemistry,* 14B (6): 411-414, 1976.
Mix et al., "A synthetic triterpenoid selectively inhibits the induction of matrix metalloproteinases 1 and 13 by inflammmatory cytokines," *Arthritis Rheum.,* 44:1096-1104, 2001.
Moncada et al., "Nitric oxide: physiology, pathophysiology, and pharmacology," *Pharmacol. Rev.,* 43:109-142, 1991.
Murray and Zweifel, "Preparation of Phenyl Cyanate and its Utilization for the Synthesis of α, β-Unsaturated Nitriles," *Synthesis,* 150-151, 1980.
Muzart, "Synthesis of unsaturated carbonyl compounds via a chromium-mediated allylic oxidation by 70% tert.butylhydroperoxide," *Tetrahedron Lett.,* 28:4665-4668, 1987.
Na and Surh et al., "Transcriptional regulation via cysteine thiol modification: a novel molecular strategy for chemoprevention and cytoprotection," *Mol. Carcinog.,* 45 (6): 368-380, 2006.
Nathan and Xie, "Nitric oxide synthases: roles, tolls, and controls," *Cell,* 78:915-918, 1994.
Nicholson et al., "Lethality of endotoxin in mice genetically deficient in the respiratory burst oxidase, inducible nitric oxide synthase, or both, " *Shock,* 11:253-258, 1999.
Nishino et al., "Inhibition of the tumor-promoting action of 12-O tetradecanoylphorbol-13-acetate by some oleanane-type triterpenoid compounds," *Cancer Res.,* 48:5210-5215, 1988.
Notice of Allowance and Fees, issued in related U.S. Appl. No. 11/121,316, mailed Apr. 30, 2010.
Office Action issued in Canadian Application No. 2,335,505, mailed Sep. 22, 2008.
Office Action issued in Canadian Application No. 2,335,505, mailed Nov. 23, 2006.
Office Action issued in Canadian Application No. 2,335,505, mailed Jan. 10, 2008.
Office Action issued in European Application No. 99 928 731.1, mailed Dec. 15, 2004.
Office Action issued in European Application No. 99 928 731.1, mailed Feb. 14, 2007.
Office Action issued in European Application No. 99 928 731.1, mailed Aug. 1, 2008.
Office Action issued in U.S. Appl. No. 11/927,418, dated Mar. 2, 2009.
Office Action issued in U.S. Appl. No. 11/927,418, dated Nov. 1, 2010.
Office Action issued in U.S. Apppl. No. 11/927,418, dated Jun. 16, 2009.
Office Action, in Canadian Patent App. No. 2,335,505, mailed May 4, 2009.
Office Action, in European Patent App. No. 99 928 731, mailed Dec. 9, 2008.
Office Action, in U.S. Appl. No. 09/335,003, mailed Aug. 28, 2000.
Office Action, in U.S. Appl. No. 09/335,003, mailed Mar. 15, 2001.
Office Action, in U.S. Appl. No. 09/335,003, mailed Nov. 2, 2000.
Office Action, in U.S. Appl. No. 09/927,081, mailed Feb. 22, 2002.
Office Action, in U.S. Appl. No. 10/395,372, mailed Apr. 28, 2006.
Office Action, in U.S. Appl. No. 10/395,372, mailed Aug. 4, 2005.
Office Action, in U.S. Appl. No. 10/395,372, mailed Dec. 20, 2006.
Office Action, in U.S. Appl. No. 10/395,372, mailed Feb. 7, 2007.
Office Action, in U.S. Appl. No. 10/395,372, mailed Jan. 28, 2004.

(56) References Cited

OTHER PUBLICATIONS

Office Action, in U.S. Appl. No. 10/395,372, mailed Jul. 9, 2004.
Office Action, in U.S. Appl. No. 10/395,372, mailed Jun. 12, 2006.
Office Action, in U.S. Appl. No. 10/395,372, mailed May 23, 2005.
Office Action, in U.S. Appl. No. 10/395,372, mailed Nov. 23, 2005.
Office Action, in U.S. Appl. No. 11/121,316, mailed Apr. 16, 2009.
Office Action, in U.S. Appl. No. 11/121,316, mailed Jul. 21, 2008.
Office Action, in U.S. Appl. No. 11/121,316, mailed Mar. 17, 2008.
Ohshima and Bartsch, "Chronic infections and inflammatory process as cancer risk factors: possible role of nitric oxide in carcinogenesis," *Mutat. Res.*, 305:253-264, 1994.
Omura and Swern, "Oxidation of Alcohols by 'Activated' Dimethyl Sulfoxide. A Preparative Steric and Mechanistic Study," *Tetrahedron*, 34:1651-1660, 1978.
Ono et al., "A convenient procedure for esterification of carboxylic acids," *Bull. Chem. Soc. Jpn.*, 51:2401-2404, 1978.
Oshima et al., "Suppression of intestinal polyposis in Apc$^{\Delta 716}$ knock-out mice by inhibition of cyclooxygenase 2 (COX-2)," *Cell*, 87:803-809, 1996.
Osman et al., "Application of chemical reactions on thin-layer chromatoplates. IV. Triterpene," *Bulletin of the Chemical Society of Japan*, 47 (8): 2056-2058, 1974.
Osman et al., "Chemical studies on pentacyclic triterpenes. I. Benzilic acid rearrangement of ring A in ursolic acid," *Egyptian J. of Chemistry*, 15 (3): 269-272, 1972.
Pahl, "Activators and target genes of Rel/NF-κb transcription factors," *Oncogene*, 18:6853-6866, 1999.
Palcy and Goltzman, "Protein kinase signalling pathways involved in the up-regulation of the rat alpha1(I) collagen gene by transforming growth factor beta 1 and bone morphogenetic protein 2 in osteoblastic cells," *Biochem. J.*, 343:21-27, 1999.
PCT, International Preliminary Examination Report, in Int. App. No. PCT/US1999/13635, mailed Sep. 6, 2000.
PCT, International Search Report, in Int. App. No. PCT/US1999/13635, mailed Oct. 20, 1999.
PCT, Written Opinion, in Int. App. No. PCT/US1999/13635, mailed May 15, 2000.
Picard et al., "Structure of the triterpenes," *J. Soc. Chem. Ind.*, 58: 58-59, 1939.
Picard et al., "The triterpene resinols and related acids, part VI," *J. Chem. Soc.*, 1045-108, 1939.
Pitzele, "Synthesis of 2-oxygenated glycyrrhetic acid derivatives," *J. Of Medicinal Chemistry*, 117 (2): 191-194, 1974.
Pradhan and De, "Preparation of triterpenoid diosphenol via oximinoketone and structure of baccatin," *Indian J. Of Chemistry, Section B: Organic Chemistry including Medicinal Chemistry*, 21B (9): 823-828, 1982.
Pradhan and Ghosh, "Studies on reactions of 2-bromo-3-ketotriterpenoids: Part IV. Debromination and dehydrobromination of 2α-bromo and 2,2-dibromo derivatives of lupanone and methyl dihydrobetulonate," *Indian J. Of Chemistry, Section B: Organic Chemistry including Medicinal Chemistry*, 33B (1): 73-75, 1994.
Prescott and White, "Self-promotion? Intimate connections between APC and prostaglandin H synthase-2," *Cell*, 87:783-786, 1996.
Rayet and Gelinas, "Aberrant rel/nfkb genes and activity in human cancer," *Oncogene*, 18:6938-6947, 1999.
Reddy et al., "Evaluation of cyclooxygenase-2 inhibitor for potential chemopreventive properties in colon carcinogenesis," *Cancer Res.*, 56(20):4566-4569, 1996.
Response filed in Canadian Application No. 2,335,505, mailed Jul. 10, 2008.
Response filed in Canadian Application No. 2,335,505, mailed May 11, 2007.
Response filed in European Application No. 99 928 731.1, mailed Aug. 14, 2007.
Response filed in European Application No. 99 928 731.1, mailed Jun. 23, 2005.
Response filed in European Application No. 99 928 731.1, mailed Oct. 1, 2008.
Response to Office Action issued in U.S. Appl. No. 11/927,418, dated Oct. 16, 2009.
Response to Office Action issued in U.S. Appl. No. 11/927,418, dated Apr. 2, 2009.
Response to Office Action issued in U.S. Appl. No. 11/927,418, dated Feb. 1, 2011.
Response to Office Action, in Canadian Patent App. No. 2,335,505, dated Mar. 23, 2009.
Response to Office Action, in European Patent App. No. 99 928 731, dated Mar. 9, 2009.
Response to Office Action, in U.S. Appl. No. 09/335,003, dated Sep. 28, 2000.
Response to Office Action, in U.S. Appl. No. 09/335,003, dated Mar. 2, 2001.
Response to Office Action, in U.S. Appl. No. 09/335,003, dated Apr. 16, 2001.
Response to Office Action, in U.S. Appl.. No. 09/927,081, dated Jun. 24, 2002.
Response to Office Action, in U.S. Appl. No. 10/395,372, dated Apr. 28, 2004.
Response to Office Action, in U.S. Appl. No. 10/395,372, dated Nov. 9, 2004.
Response to Office Action, in U.S. Appl. No. 10/395,372, dated Jul. 25, 2005.
Response to Office Action, in U.S. Appl. No. 10/395,372, dated Nov. 23, 2005.
Response to Office Action, in U.S. Appl. No. 10/395,372, dated Apr. 21, 2006.
Response to Office Action, in U.S. Appl. No. 10/395,372, dated Oct. 12, 2006.
Response to Office Action, in U.S. Appl. No. 10/395,372, dated Jan. 12, 2007.
Response to Office Action, in U.S. Appl. No. 10/395,372, dated Feb. 14, 2007.
Response to Office Action, in U.S. Appl. No. 11/121,316, dated Apr. 4, 2008.
Response to Office Action, in U.S. Appl. No. 11/121,316, dated Dec. 19, 2008.
Response to Office Action, in U.S. Appl. No. 11/672,449, dated Dec. 15, 2008.
Response to Written Opinion, in Int. App. No. PCT/US1999/13635, dated Jul. 14, 2000.
Robbins et al., "Inflammation and Repair," *In*: Basic Pathology 3rd Edition, W.B. Saunders Company, Chapter 2, p. 28, 1981.
Rossi et al., "Anti-inflammatory cyclopentenone prostaglandins are direct inhibitors of IkappaB kinase," *Nature*, 403:103-108, 2000.
Ruvolo et al., "The novel triterpenoid methyl-CDDo inhibits Bcl2 phosphorylation and potently kolls U937 cells," *Blood*, 94(10), Suppl. 1, Part 1: 280A, abstract #1251, 1999.
Salvemini et al., "Endogenous nitric oxide enhances prostaglandin production in a model of renal inflammation," *J. Clin. Invest.*, 93(5):1940-1947, 1994.
Salvemini et al., "Nitric oxide activates cyclooxygenase enzymes," *Proc. Natl. Acad. Sci. USA*, 90(15):7240-7244, 1993.
Seibert and Masferrer, "Role of inducible cyclooxygenase (COX-2) in inflammation," *Receptor*, 4(1):17-23, 1994.
Sejbal et al., "Triterpenes. Part LXXIII. Reactions of triterpenoid ketones with sulfur and morpholine under Willgerodt-Kindler reaction conditions," *Collection of Czechoslovak Chemical Communications*, 51 (1): 118-127, 1986.
Sejbal et al., "Triterpenes. Part XC. Conversion of betulin into careyagenolide (2α,3β- dihydroxy-18α, 19βH-ursan-28, 20β-olide," *Collection of Czechoslovak Chemical Communications*, 54 (4): 1036-1042, 1989.
Sharpless et al., "Electrophilic and nucleophilic organoselenium reagents. New routes to alpha, beta-unsaturated carbonyl compounds," *J. Am. Chem. Soc.*, 95:6137, 1973.

(56) References Cited

OTHER PUBLICATIONS

Sheng et al., "A selective cyclooxygenase 2 inhibitor suppresses the growth of H-ras-transformed rat intestinal epithelial cells," *Gastroenterology*, 113(6):1883-18891, 1997.
Sheng et al., "Inhibition of human colon cancer cell growth by selective inhibition of cyclooxygenase-2," *J. Clin. Invest.*, 99(9):2254-2259, 1997.
Shimao and Oae, "Activity coefficients of dimethyl-β-cyclodextrin in aqueous solution," *Bulletin of the Chemical Society of Japan*, 56 (2): 643-644, 1983.
Shull et al., "Identification of a vitamin D-responsive protein on the surface of human osteosarcoma cells," *Proc. Natl. Acad. Sci. USA*, 86:5405-5410, 1989.
Shull et al., "Morphologic and biochemical studies of canine mucopolysaccharidosis I," *Am. J. Pathol.*, 114:487-495, 1984.
Simonian and Coyle, "Oxidative stress in neurodegenerative diseases," *Annu. Rev. Pharmacol. Toxicol.*, 36:83-106, 1996.
Simonsen et al., "Tetracyclic hydroxy acids," In *the Terpenes*, Cambridge University, Cambridge, 5:221-285, 1957.
Singh and Evans, "Nitric oxide, the biological mediator of the decade: fact or fiction?" *Eur. Respir. J.*, 10:699-707, 1997.
Singh et al., "Anti-inflammatory activity of oleanolic acid in rats and mice," *J. Pharm.Pharmacol.*, 44:456-458, 1992.
Snitman et al., "Synthetic approaches to taxodione synthesis of methyl 12-oxopodocarpa-5,9(11)-diene-8β-carboxylate," *Synth. Comm.*, 8:187-194, 1978.
Sonogashira et al., "A convenient synthesis of acetylenes: catalytic substitutions of acetylenic hydrogen with bromoakenes, iodoarenes, and bromopyridines," *Tetrahedron Lett.*, 4467-4470, 1975.
Sporn and Roberts, "Peptide growth factors and inflammation, tissue repair, and cancer," *J. Clin. Invest.*, 78:329-332, 1986.
Sporn et al., "Prospects for prevention and treatment of cancer with selective PPARγ modulators (SPARMs)," *Trends in Molecular Medicine*, 7(9):395-400, 2001.
Sporn et al., "Transforming growth factor-β: biological function and chemical structure," *Science*, 233:532-534, 1986.
Steadman's Medical Journal 23rd Edition, The Williams & Wilkins Company, p. 401, 1976.
Sterzycki, "Pyrodinium tosylate, a mild catalyst for formation and cleavage of dioxolane-type acetals," *Synthesis*, 724-725, 1979.
Strejan et al., "Suppression of chronic-relapsing experimental allergic encephalomyelitis in strain-13 guinea pigs by administration of liposome-associated myelin basic protein," *J. Neuroimmunol.*, 7 (1): 27, 1984.
Suh et al., "A novel synthetic oleanane triterpenoid, 2-cyano-3,12-dioxoolean-1,9-dien-28-oic acid (CDDO), induces cell differentiation in human myeloid leukemias," *Proceedings of the American Association for Cancer Research Annual Meeting*, 40:300, abstract # 1988, 1999.
Suh et al., "A novel synthetic oleanane triterpenoid, 2-cyano-3,12-dioxoolean-1,9-dien-28-oic acid, with potent differentiating, antiproliferative, and anti-inflammatory activity," *Cancer Res.*, 59(2):336-341, 1999.
Suh et al., "New triterpenoids as cancer preventive and anti-inflammatory agents," *Proceedings of the American Association for Cancer Research*, Abstract No. 1457, 38: 216, 1997.
Suh et al., "New triterpenoids as cancer preventive and anti-inflammatory agents," 88th AACR Meeting, San Francisco, California, abstract No. 1457, Mar. 1997.
Suh et al., "New triterpenoids as cancer preventive and anti-inflammatory agents," 88th AACR Meeting, San Francisco, California, poster, Mar. 1997.
Suh et al., "Novel triterpenoids suppress inducible nitric oxide synthase (INOS) and inducible cyclooxygenase (COX-2)," 89th AACR Meeting, New Orleans, Louisiana, slides from oral presentation, Mar. 28-Apr. 1, 1998.
Suh et al., "Novel triterpenoids suppress inducible nitric oxide synthase (iNOS) and inducible cyclooxygenase (COX-2) in mouse macrophages," *Cancer Res.*, 58:717-723, 1998.
Suh et al., "Novel triterpenoids suppress inducible ntiric oxide synthase (iNOS) and inducible cyclooxygenase (COX-2)," Proceedings of the American Association for Cancer Research Annual Meeting, 39:266, 1998.
Sun et al., "The synthetic triterpenoid, CDDO, suppresses alloreactive T cell responses and reduces murine early acute graft-versus-host disease mortality," *Biology of Blood and Marrow Transplantation*, 13:521-529, 2007.
Syftestad et al., "The in vitro chondrogenic response of limb-bud mesenchyme to a water-soluble fraction prepared from demineralized bone matrix," *Differentiation*, 29:230, 1985.
Takabe et al., "Synthesis of lycosyl esters of oleanolic," *Carbohydrate Research*, 76:101-108, 1979, Database CAPLUS on STN AN:1980:42278.
Takahashi et al., "Increased expression of inducible and endothelial constitutive nitric oxide synthases in rat colon tumors induced by azoxymethane," *Cancer Res.*, 57:1233-1237, 1997.
Tamir and Tannebaum, "The role of nitric oxide (NO) in the carcinogenic process," *Biochim. Biophys. Acta*, 1288:F31-F36, 1996.
Tamm et al., "Expression and prognostic significance of IAP-family genes in human cancers and leukemias," *Blood*, 94(Suppl. 1):69a, Abstract # 298, 1999.
Tenenbaum and Heersche, "Differentiation of osteoblasts and formation of mineralized bone in vitro," *Calcif. Tissue Int.*, 34:76, 1982.
Toriumi et al., "Mandibular reconstruction with a recombinant bone-inducing factor. Functional, histologic, and biomechanical evaluation," *Arch. Otolaryngol. Head Neck Surg.*, 117:1101-1112, 1991.
Tsai et al., "Monoclonal antibody to human osteosarcoma: a novel $M_r$ 26,000 protein recognized by murine hybridoma TMMR-2," *Cancer Res.*, 50:152-161, 1990.
Tsujii and DuBois, "Alterations in cellular adhesion and apoptosis in epithelial cells overexpressing prostaglandin endoperoxide synthase 2," *Cell*, 83:493-501, 1995.
Tsujii et al., "Cyclooxygenases regulates angiogenesis induced by colon cancer cells," *Cell*, 93:705-716, 1998.
Turksen et al., "Isolation of monoclonal antibodies recognizing rat bone-associated molecules in vitro and in vivo," *J. Histochem. Cytochem.*, 40:1339-1352, 1992.
Vazquez et al., "Human immunodeficiency virus type 1-induced macrophage gene expression includes the p21 gene, a target for viral regulation," *J. Virol.*, 79:4479-4491, 2005.
Veerman et al., "Antitumor activity of prolonged as compared with bolus administration of 2',2'-difluorodeoxycytidine in vivo against murine colon tumors," *Cancer Chemother. Pharmacol.*, 38 (4): 335-342, 1996.
Vodovotz et al., "Inducible nitric oxide synthase in tangle-bearing neurons of patients with Alzheimer's Disease," *The Journal of Experimental Medicine*, 184:1425-1433, 1996.
Vukicevic et al., "Stimulation of the expression of osteogenic and chondrogenic phenotypes in vitro by osteogenin," *Proc. Natl. Acad. Sci. USA*, 86:8793-7, 1989.
Walczak et al., "Tumoricidal activity of tumor necrosis factor-related apoptosis-inducing ligand in vivo", *Nature Medicine*, 5(2):157-163, 1999.
Walsh et al., "Monoclonal antibodies with selective reactivity against osteoblasts and osteocytes in human bone," *J. Bone Miner Res.*, 9:1687-1696, 1994.
Wang et al., "A novel synthetic triterpenoid, 2-cyano-3,12-dioxoolean-1,9-dien-28-oic acid (CDDO) induces adipocyte differentiation in 3T3-L1 cells," *Proceedings of the American Association for Cancer Research Annual Meeting*, 40:300, abstract # 1989, 1999.
Wang et al., "A synthetic triterpenoid, 2-cyano-3,12-dioxooleana-1,9-dien-28-oic acid (CDDO), is a ligand for the peroxisome proliferator-activated receptor γ," *Mol. Endocrinol.*, 14:1550-1556, 2000.
Warrell et al., "Differentiation therapy of acute promyelocytic leukemia with tretinoin (alltrans-retinoic acid)," *N. Engl. J. Med.*, 324(20):1385-1393, 1991.
Williams et al., "Immunology of multiple sclerosis," *Clin. Neurosci.*, 2(3-4):229-245, 1994.

(56) References Cited

OTHER PUBLICATIONS

Witz et al., "Cyclic ketones. XIII. Circular dichroism of steroid and triterpene ketones. Conformation of ring A of 8-methylated 3-oxotriterpenes," *Bull. Soc. China,* France: 1101-1112, 1963. (French only, but see attached English CAPLUS database summary.).

Woodley, "Liposomes for oral administration of drugs," Critical Reviews in Therapeutic Drug Carrier System, 2:1-18, 1995.

Xie et al., "Differential expression patterns in human myeloblastic leukemia HL-60 and multidrug resistant HL-60/Dox cells analyzed by human cDNA expression array," *Blood,* 92 (Suppl 1):387a, Abstract #1600. 1998.

English Translation of Office Communication issued in corresponding Japanese Patent Application No. 2009-136739, dated May 28, 2012.

* cited by examiner

THERAPEUTIC COMPOUNDS AND METHODS OF USE

The present application is a continuation of U.S. patent application Ser. No. 11/927,418 filed Oct. 29, 2007 now U.S. Pat. No. 8,034,955, which is a continuation of U.S. patent application Ser. No. 10/395,372 filed Mar. 24, 2003, now U.S. Pat. No. 7,288,568 issued Oct. 30, 2007, which is a continuation of U.S. patent application Ser. No. 09/927,081 filed Aug. 9, 2001, now U.S. Pat. No. 6,552,075 issued Apr. 22, 2003, which is a divisional of U.S. patent application Ser. No. 09/335,003 filed Jun. 17, 1999, now U.S. Pat. No. 6,326,507 issued Dec. 4, 2001, which claims the benefit of priority to U.S. Provisional Application No. 60/090,053 filed Jun. 19, 1998, the entire contents of which are incorporated herein by reference. Additionally, all patents, published patent applications, and other references cited throughout this specification are hereby incorporated by reference in their entireties.

This invention was made with government support under grant numbers CA-23108, RO1 CA 54494, RO1 CA 62275, KO1 CA 75154 and NS 28767, awarded by the National Institutes of Health, and DOD/AMRD award number 1796-1-6163, awarded by the Department of Defense. The government has certain rights in the invention.

BACKGROUND OF THE INVENTION

The present invention relates to compounds which have been found to be useful for prevention or treatment of diseases such as cancer, Alzheimer's disease, Parkinson's disease, multiple sclerosis, rheumatoid arthritis, and other inflammatory diseases.

One of the major needs in cancer prevention is the development of effective and safe new agents for chemoprevention. In particular, there is a need for chemopreventative agents targeted at mechanisms known to be involved in the process of carcinogenesis. In recent years, there has been a resurgence of interest in the study of mechanisms of inflammation that relate to carcinogenesis and in the use of such mechanisms as the basis for development of new chemopreventative agents.

The concept that inflammation and carcinogenesis are related phenomena has been the subject of many studies that have attempted to link these two processes in a mechanistic fashion (Sporn and Roberts, 1986; Ohshima and Bartsch, 1994). The enzymes that mediate the constitutive synthesis of NO and prostaglandins from arginine and arachidonate, respectively, have relative little significance for either inflammation or carcinogenesis. In contrast, inducible nitric oxide synthase (iNOS) and inducible cyclooxygenase (COX-2) both have critical roles in the response of tissues to injury or infectious agents (Moncada et al., 1991; Nathan and Xie, 1994; Siebert and Masferrer, 1994; Tamir and Tannebaum, 1996). These inducible enzymes are essential components of the inflammatory process, the ultimate repair of injury, and carcinogenesis. While physiological activity of iNOS and COX-2 may provide a definite benefit to the organism, aberrant or excessive expression of either iNOS or COX-2 has been implicated in the pathogenesis of many disease processes, particularly in chronic degeneration of the central nervous system, carcinogenesis, septic shock, cardiomyopathy, and rheumatoid arthritis.

Triterpenoids, biosynthesized in plants by the cyclization of squalene, are used for medicinal purposes in many Asian countries; and some, like ursolic and oleanolic acids, are known to be anti-inflammatory and anti-carcinogenic (Huang et al., 1994; Nishino et al., 1988). However, the biological activity of these naturally occurring molecules is relatively weak, and therefore the synthesis of new analogs to enhance their potency was undertaken (Honda et al., 1997; Honda et al., 1998). It was previously reported that several such synthetic analogs can suppress the de novo formation of iNOS and COX-2 in macrophages that have been stimulated by IFN-γ or LPS (Suh et al., 1998). The role of both iNOS and COX-2 as enhancers of carcinogenesis in many organs is receiving increasing attention (Ohshima et al., 1994; Tamir et al., 1996; Takahashi et al., 1997; Ambs et al., 1998; Tsujii et al., 1998; Oshima et al., 1996; Hida et al., 1998; Huang et al., 1998); suppression of either the synthesis or the activity of these enzymes is therefore a target for chemoprevention (Oshima et al., 1998; Kawamori et al., 1998). Agents which induce differentiation or suppress proliferation of premalignant or malignant cells represent yet another mechanistic approach to chemoprevention, as well as to chemotherapy, of cancer.

SUMMARY OF THE INVENTION

The present invention provides methods and compositions for the prevention or treatment of diseases such as cancer, Alzheimer's disease, Parkinson's disease, and multiple sclerosis. The methods of the invention involve administering to a subject a therapeutic compound of the formula:

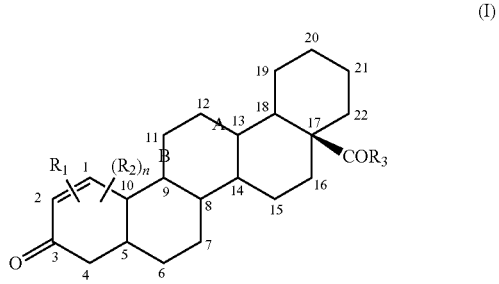

(I)

wherein A or B is a single or double bond and $C_{11}$ or $C_{12}$ have substituted thereon =X which is an organic or inorganic moiety; $R_1$ is an organic or inorganic moiety which may be substituted anywhere on the six-membered ring denoted by positions 1 through 10; $R_2$ and $R_3$ are hydrogen or organic or inorganic moieties, wherein an $R_2$ group may be substituted anywhere on the structure represented in the formula; and n is a number from 0 to 100.

The invention further relates to therapeutic compositions and methods of their use having the formula

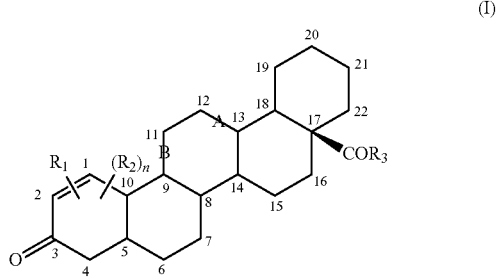

(I)

wherein either A or B is a double bond such that when A is a double bond, $C_{11}$ has substituted thereon =X which is an organic or inorganic moiety and when B is a double bond, $C_{12}$ has substituted thereon =X; $R_1$ is an organic or inorganic moiety which may be substituted anywhere on the six-membered ring denoted by positions 1 through 10; $R_2$ and $R_3$ are hydrogen or organic or inorganic moieties, wherein an $R_2$ group may be substituted anywhere on the structure represented in formula (I); and n is a number from 0 to 100).

Accordingly, in an embodiment the compositions and methods of the invention are useful for prevention or treatment of disorders such as cancer; neurodegenerative diseases (NDDs) such as Parkinson's disease (PD), Alzheimer's disease (AD), multiple sclerosis (MS), and amyotrophic lateral sclerosis (ALS); inflammatory diseases, e.g., inflammatory bowel diseases such as Crohn's disease and ulcerative colitis; and rheumatoid arthritis (RA). The methods of the invention can be used therapeutically to prevent or treat such conditions in a subject. The methods are based, at least in part, on the discovery that the presently disclosed compounds have been found to suppress transcription or translation of iNOS and COX-2 genes, the overexpression of which is linked with excess NO and/or prostaglandin formation.

In a further aspect the invention relates to triterpenoid compositions effective for modulating interferon-γ (IFN-γ)-induced NO production in macrophages, said composition having an $IC_{50}$ value of at least less than 0.6 µM, preferably less than 0.001 µM.

In another aspect a method of preventing or treating a disorder characterized by overexpression of iNOS or COX-2 genes is presented, comprising administering to a subject a pharmaceutically effective amount of a composition of formula (I), such that the disorder is prevented or treated. Such disorders include cancer; neurodegenerative diseases such as Parkinson's disease, Alzheimer's disease, multiple sclerosis, and amyotrophic lateral sclerosis; and rheumatoid arthritis.

In a further aspect a method of modulating transcription or translation of iNOS or COX-2 genes in a subject comprises administering to a subject a pharmaceutically effective amount of a composition of formula (I), such that the transcription or translation of iNOS or COX-2 genes is modulated.

In yet another aspect a method of modulating excessive nitric oxide or prostaglandin formation in a subject is presented, comprising administering to a subject a pharmaceutically effective amount of a composition of formula (I), such that nitric oxide or prostaglandin formation is modulated.

DETAILED DESCRIPTION OF THE INVENTION

Figure 1:
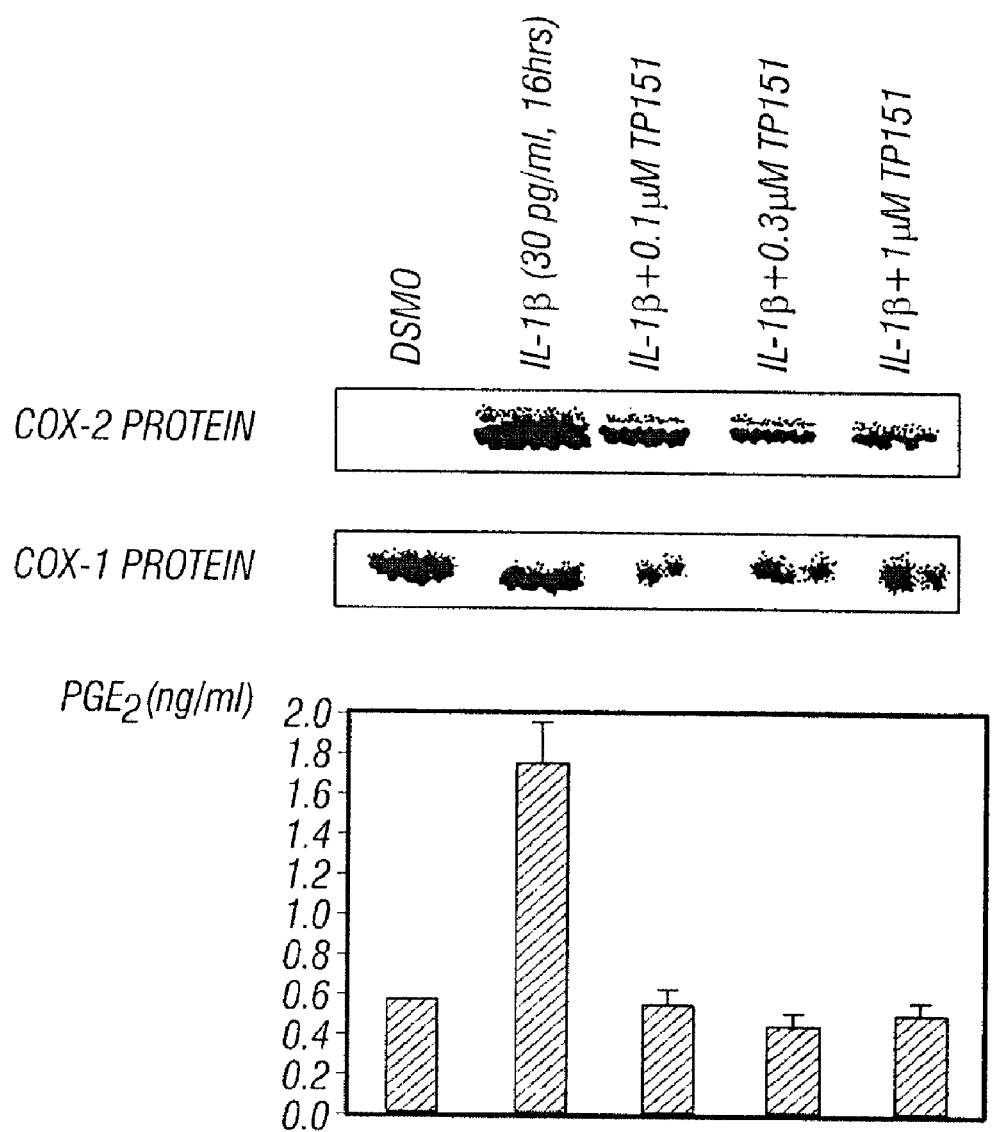
FIG. 1 illustrates the efficacy of a composition of the invention, 2-cyano-3,12-dioxoolean-1,9-dien-28oic acid (CDDO) (denoted "TP-151"), in supressing interleukin-1β (IL-1β)-induced COX-2 expression and prostaglandin $E_2$ ($PGE_2$) in human colon myofibroblast [18]Co cells.
Figure 2:
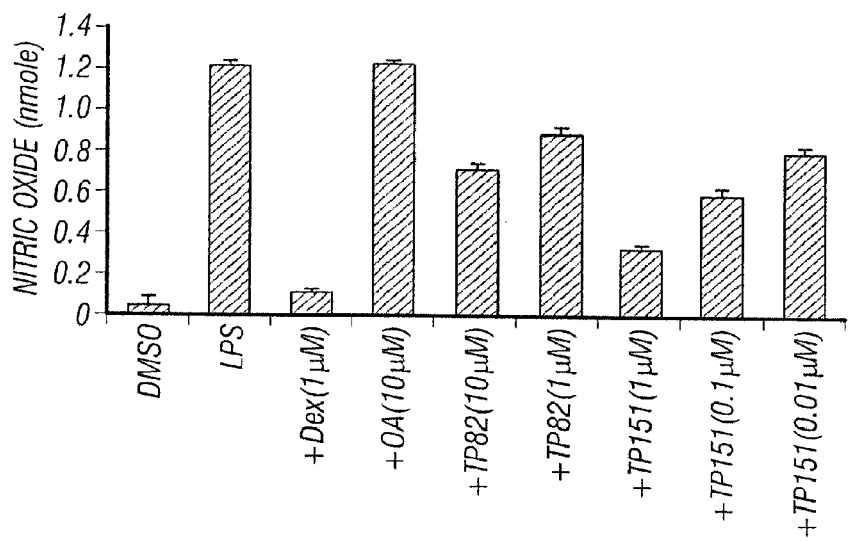
FIG. 2 is a comparison of the efficacy of various compounds on NO production induced by lipopolysaccharide (LPS) in rat microglia cells (brain macrophage cells), showing activity of TP151 favorable to that of dexamethasone, a glucocorticoid, thus indicating how a composition of the invention may be used to prevent or treat a neurodegenerative disease. "TP-82" refers to 3,11-dioxoolean-1,9-dien-28oic acid.
Figure 3:
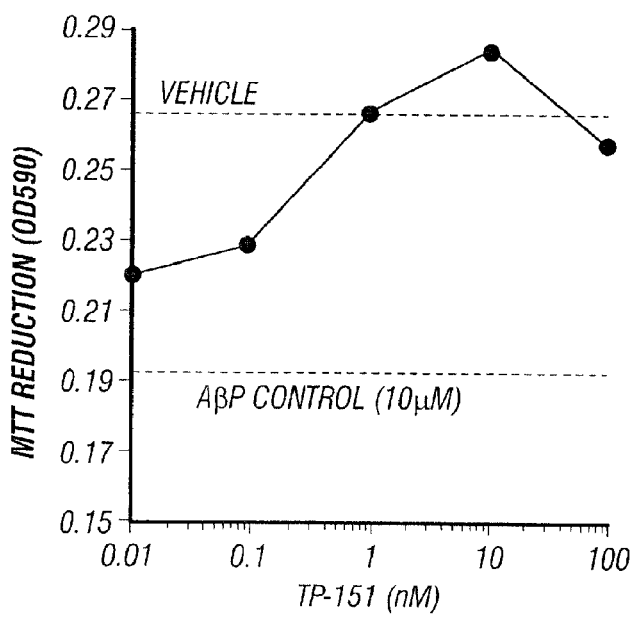
FIG. 3 illustrates the efficacy of TP151 in protecting in rat hippocampal neurons against toxicity induced by β-amyloid peptide, which is implicated in Alzheimer's disease.
Figure 4:
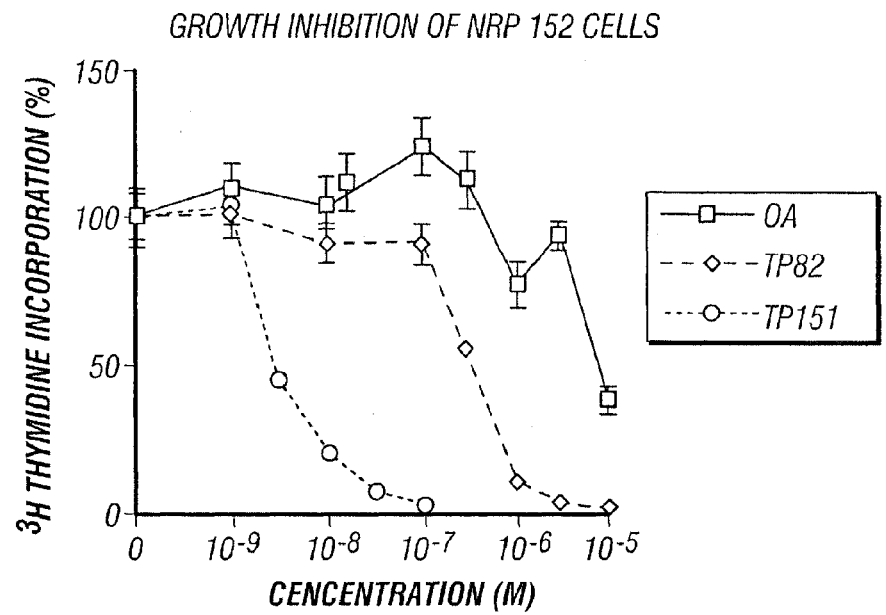
FIG. 4 illustrates, relevant to prevention or treatment or prostate cancer, the efficacy of TP151 in inhibiting growth of normal rat prostate cells (NRP152)
Figure 5:
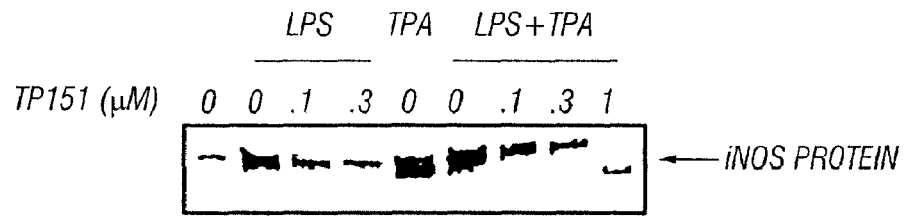
FIG. 5 illustrates the efficacy of TP151 in modulating expression of iNOS protein in normal rat prostate cells (NRP152)
Figure 6:
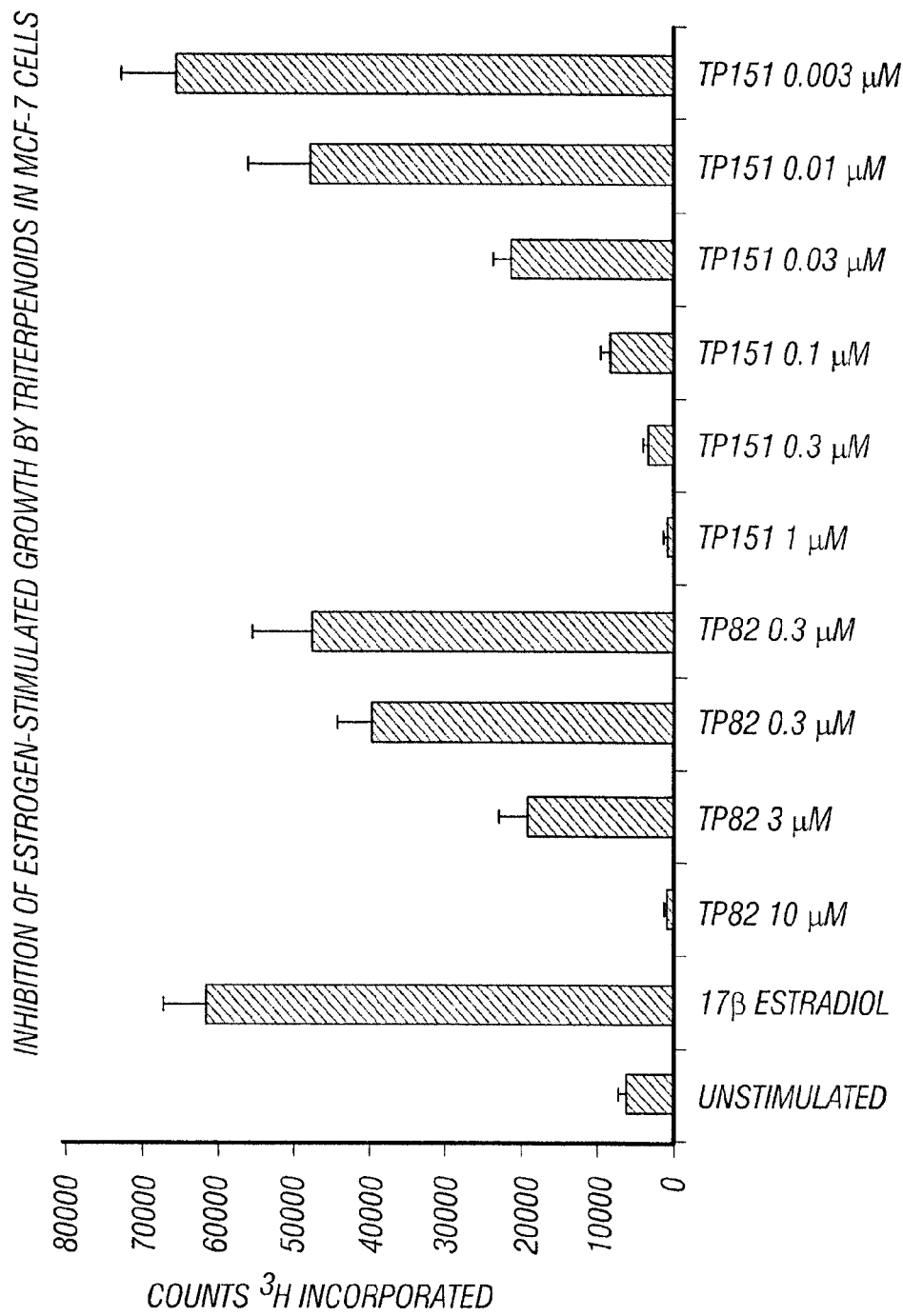
FIG. 6 illustrates, relevant to prevention or treatment or breast cancer, a comparison of the efficacy of various compounds including TP151 in inhibiting estrogen-stimulated growth in MCF-7 cells (breast cancer cell line)
Figure 7:
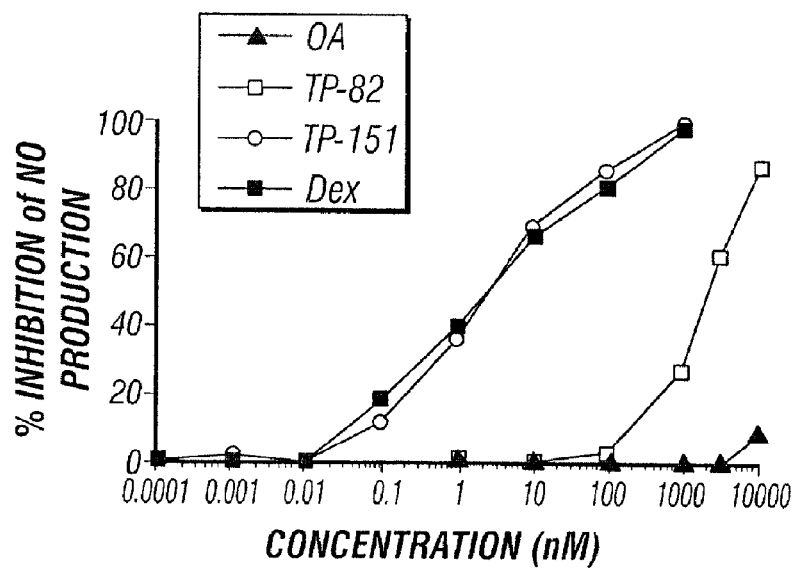
FIG. 7 illustrates, relevant to prevention or treatment of conditions with an inflammatory component, a comparison of the efficacy of various compounds on inhibiting NO production induced by LPS and IFN-γ in primary mouse macrophages, showing activity of TP151 favorable to that of dexamethasone.
Figure 8:
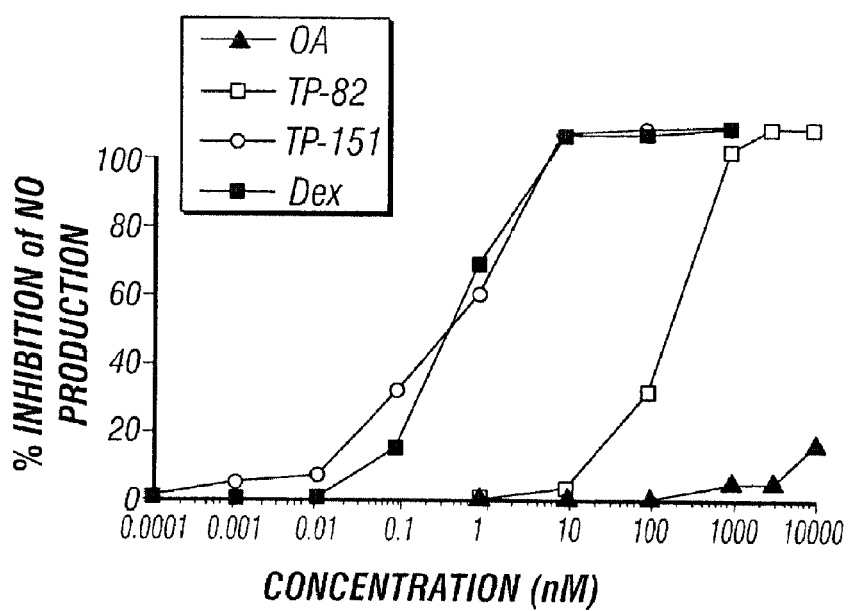
FIG. 8 is a comparison of the efficacy of various compounds on inhibiting NO production induced by IFN-γ in primary mouse macrophages.
Figure 9:
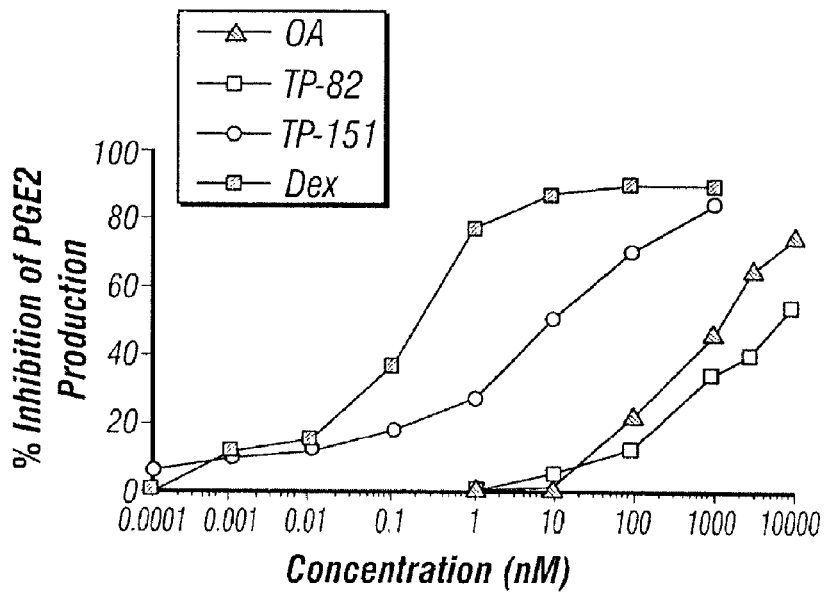
FIG. 9 illustrates a comparison of the efficacy of various compounds on inhibiting $PGE_2$ production induced by LPS and IFN-γ in primary mouse macrophages.
Figure 10:
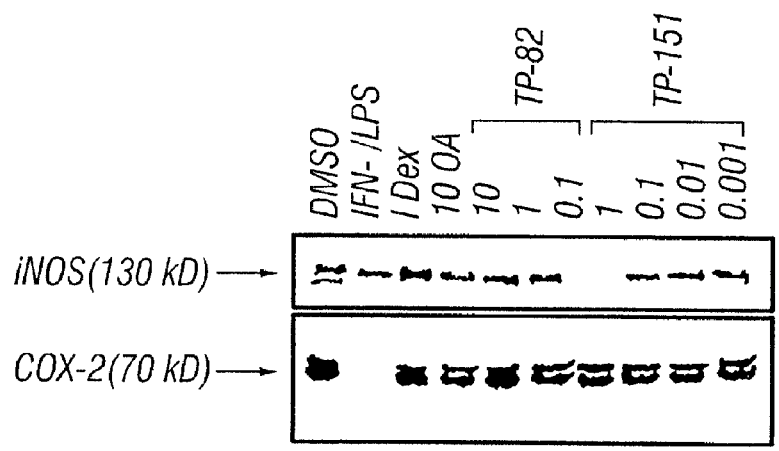
FIG. 10 illustrates a comparison of the efficacy of various compounds on suppressing IFNγ and LPS-induced iNOS and COX-2 expression in primary mouse macrophages.

Before further description of the invention, certain terms employed in the specification, examples and appended claims are, for convenience, collected here.

Definitions

As used herein, the term "organic moiety" is intended to include carbon based functional groups such as alkyl, alkylamino, alkoxy, aryl, aralkyl, aryloxy, alkylthio, and alkylcarboxyl.

As used herein, the term "inorganic moiety" is intended to include non carbon-based groups or elements such as hydrogen, halo, amino, nitro, thiol, and hydroxyl.

As used herein, the term "electron withdrawing moiety" is known in the art, and refers to a group which has a greater electron-withdrawing than hydrogen. A variety of electron-withdrawing groups are known, and include halogens (e.g., fluoro, chloro, bromo, and iodo groups), nitro, cyano, $-NR_3^+$, $-SR_2^+$, $-NH_3^+$, $-SO_2R$, $-SO_2Ar$, $-COOH$, $-OAr$, $-COOR$, $-OR$, $-COR$, $-SH$, $-SR$, $-OH$, $-Ar$, and $-CH=CR_2$, where Ar is aryl, and R represents any appropriate organic or inorganic moiety and, preferably, alkyl moiety.

As used herein, the term "halosubstituted alkyl moieties" is intended to include alkyl moieties which have halogen moieties in the place of at least one hydrogen.

As used herein, the term "amino" means $-NH_2$; the term "nitro" means $-NO_2$; the term "halogen" designates $-F$, $-Cl$, $-Br$ or $-I$; the term "thiol" means SH; and the term "hydroxyl" means $-OH$. Thus, the term "alkylamino" as used herein means an alkyl group, as defined above, having an amino group attached thereto. The term "alkylthio" refers to an alkyl group, as defined above, having a sulfhydryl group attached thereto. The term "alkylcarboxyl" as used herein means an alkyl group, as defined above, having a carboxyl group attached thereto.

The term "aromatic group" is intended to include unsaturated cyclic hydrocarbons containing one or more rings. Aromatic groups include 5- and 6-membered single-ring groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. The aromatic ring may be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like.

The term "alkyl" refers to the saturated aliphatic groups, including straight-chain alkyl groups, branched-chain alkyl groups, cycloalkyl (alicyclic) groups, alkyl substituted cycloalkyl groups, and cycloalkyl substituted alkyl groups.

Moreover, the term "alkyl" (including "lower alkyl") as used throughout the specification and claims is intended to include both "unsubstituted alkyls" and "substituted alkyls", the latter of which refers to alkyl moieties having moieties replacing a hydrogen on one or more carbons of the hydrocarbon backbone. Such moieties can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the moieties described above. An "aralkyl" moiety is an alkyl substituted with an aryl (e.g., phenylmethyl (benzyl)).

The term "alkoxy", as used herein, refers to a moiety having the structure —O-alkyl, in which the alkyl moiety is described above.

The term "aryl" as used herein includes 5- and 6-membered single-ring aromatic groups that may include from zero to four heteroatoms, for example, unsubstituted or substituted benzene, pyrrole, furan, thiophene, imidazole, oxazole, triazole, triazole, pyrazole, pyridine, pyrazine, pyridazine and pyrimidine, and the like. Aryl groups also include polycyclic fused aromatic groups such as naphthyl, quinolyl, indolyl, and the like. The aromatic ring can be substituted at one or more ring positions with such moieties, e.g., as described above for alkyl groups. Preferred aryl groups include unsubstituted and substituted phenyl groups.

The term "aryloxy", as used herein, refers to a group having the structure —O-aryl, in which the aryl moiety is as defined above.

The term "amino," as used herein, refers to an unsubstituted or substituted moiety of the formula —$NR_aR_b$, in which $R_a$ and $R_b$ are each independently hydrogen, alkyl, aryl, or heterocyclyl, or $R_a$ and $R_b$, taken together with the nitrogen atom to which they are attached, form a cyclic moiety having from 3 to 8 atoms in the ring. Thus, the term "amino" is intended to include cyclic amino moieties such as piperidinyl or pyrrolidinyl groups, unless otherwise stated. An "amino-substituted amino group" refers to an amino group in which at least one of $R_a$ and $R_b$, is further substituted with an amino group.

As used herein, the term "subject" is intended to include living organisms in which certain conditions as described herein can occur. Examples include humans, monkeys, cows, sheep, goats, dogs, cats, mice, rats, and transgenic species thereof. In a preferred embodiment, the subject is a primate. In an even more preferred embodiment, the primate is a human. Other examples of subjects include experimental animals such as mice, rats, dogs, cats, goats, sheep, pigs, and cows. The experimental animal can be an animal model for a disorder, e.g., a transgenic mouse with an Alzheimer's-type neuropathology. A subject can be a human suffering from a neurodegenerative disease, such as Alzheimer's disease, or Parkinson's disease.

As used herein, the term "$IC_{50}$" refers to an inhibitory dose which is 50% of the maximum response obtained.

Other abbreviations used herein are as follows: CDDO, 2-cyano-3,12-dioxoolean-1,9-dien-28-oic acid; DMSO, dimethyl sulfoxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFN-γ, interferon-γ, LPS, bacterial endotoxic lipopolysaccharide; TNF-α, tumor necrosis factor-α; IL-1β, interleukin-1β, GAPDH, glyceraldehyde-3-phosphate dehydrogenase; MTT, 3-[4,5-dimethylthiazol-2-yl]-2,5-diphenyltetrazolium bromide; TCA, trichloroacetic acid.

The compounds may be administered, e.g., orally or by subcutaneous, intravenous, intraperitoneal, etc. administration (e.g. by injection). Depending on the route of administration, the active compound may be coated in a material to protect the compound from the action of acids and other natural conditions which may inactivate the compound.

To administer the therapeutic compound by other than parenteral administration, it may be necessary to coat the compound with, or co-administer the compound with, a material to prevent its inactivation. For example, the therapeutic compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., (1984) *J. Neuroimmunol.* 7:27).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a subject.

Active compounds are administered at a therapeutically effective dosage sufficient to treat a condition associated with a condition in a subject. A "therapeutically effective dosage" preferably reduces the amount of symptoms of the condition in the infected subject by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans, such as the model systems shown in the Example and Figures.

The invention features a composition of matter having the formula:

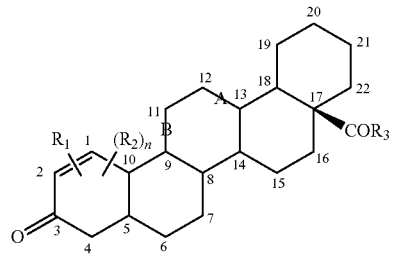

(I)

wherein A or B is a single or double bond and $C_{11}$ or $C_{12}$ have substituted thereon =X which is an organic or inorganic moiety; $R_1$ is an organic or inorganic moiety which may be substituted anywhere on the six-membered ring denoted by positions 1 through 10; $R_2$ and $R_3$ are hydrogen or organic or inorganic moieties, wherein an $R_2$ group may be substituted anywhere on the structure represented in the formula; and n is a number from 0 to 100.

The invention further features a composition of matter having the formula:

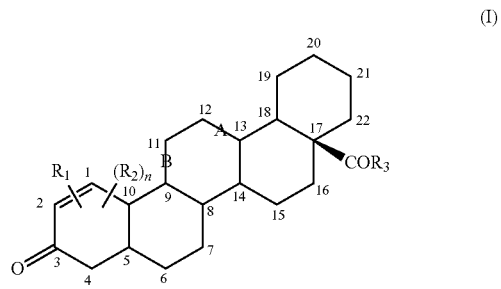

(I)

wherein either A or B is a double bond such that when A is a double bond, $C_{11}$ has substituted thereon =X which is an organic or inorganic moiety and when B is a double bond, $C_{12}$ has substituted thereon =X; $R_1$ is an organic or inorganic moiety which may be substituted anywhere on the six-membered ring denoted by positions 1 through 10; $R_2$ and $R_3$ are hydrogen or organic or inorganic moieties, wherein an $R_2$ group may be substituted anywhere on the structure represented in formula (I); and n is a number from 0 to 100).

$R_1$ may be an electron-withdrawing group, e.g., cyano, aryl, and halosubstituted alkyl moieties. Preferably, $R_1$ may include cyano, halo, or —OR', wherein R' is H or an organic moiety, e.g., acetyl or carboxyl group. R, may be substituted anywhere on the six-membered ring denoted by positions 1 through 10, but in a preferred embodiment $R_1$ is at position 2 and in a more preferred embodiment $R_1$ is a cyano group at position 2.

In a more preferred embodiment of formula (I), B is a double bond, X is O, $R_3$ is —OH, and $R_1$ is a cyano group, preferably at position 2. Examples of preferred compounds include 3,11-dioxoolean-1,12-dien-28oic acid, 2-cyano-3,11-dioxoolean-1,12-dien-28oic acid and 2-cyano-3,12-dioxoolean-1,9-dien-28oic acid.

In another aspect, the invention features a triterpenoid composition effective for modulating IFN-γ-induced NO production in macrophages, said composition having an $IC_{50}$ value of at least less than 0.6 μM, more preferably less than 0.001 μM.

In another aspect a method of preventing or treating a disorder characterized by overexpression of iNOS or COX-2 genes is presented, comprising administering to a subject a pharmaceutically effective amount of a composition of formula (I), such that the disorder is prevented or treated. In a preferred embodiment, the disorder includes cancer, neurodegenerative diseases, and rheumatoid arthritis. In a further preferred embodiment, the neurodegenerative disease includes Parkinson's disease, Alzheimer's disease, multiple sclerosis, and amyotrophic lateral sclerosis. The cancer may include breast cancer, prostate cancer, colon cancer, brain cancer, and bone cancer.

In another aspect, the invention features a method of modulating excessive nitric oxide or prostaglandin formation in a subject, comprising administering to a subject a pharmaceutically effective amount of a composition of formula (I), such that the nitric oxide or prostaglandin formation is modulated.

In another aspect, the invention features a method of modulating transcription or transcription of iNOS or COX-2 genes in a subject comprises administering to a subject a pharmaceutically effective amount of a composition of formula (I), such that the transcription or translation of iNOS or COX-2 genes is modulated.

In another aspect, the invention features a method of preventing or treating a neurodegenerative disease, comprising administering to a subject a pharmaceutically effective amount of a composition of formula (I), such that the neurodegenerative disease is prevented or treated. In a preferred embodiment, the neurodegenerative disease includes Parkinson's disease, Alzheimer's disease, multiple sclerosis, and amyotrophic lateral sclerosis.

The compounds of the present invention are compounds based on the five ring structure shown in formula (I), which, in a preferred embodiment, are based on a triterpenoid structure as shown below:

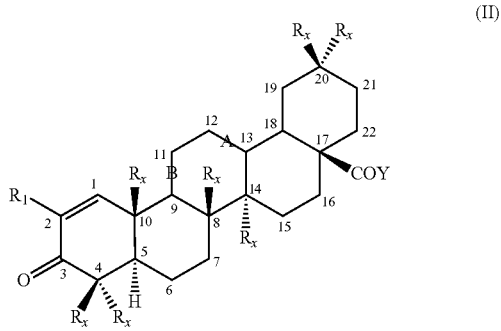

(II)

wherein $R_x$ represents any organic or inorganic moiety, preferably methyl; and Y is preferably hydroxyl. Triterpenoids, like the steroids, are formed in nature by the cyclization of squalene, with the retention of all 30 carbon atoms in molecules such as ursolic acid (UA) and oleanoic acid (OA). Although OA and UA are known to have numerous pharmacological activities, the potency of these naturally occurring molecules is relatively weak. The derivatives of OA and UA as disclosed herein, however, are more potent than OA and UA.

In a preferred embodiment, such compounds include derivatives of ursolic acid and oleanoic acid. In a particularly preferred embodiment, derivatives of OA, e.g., 2-cyano-3,12-dioxoolean-1,9-dien-28oic acid (CDDO):

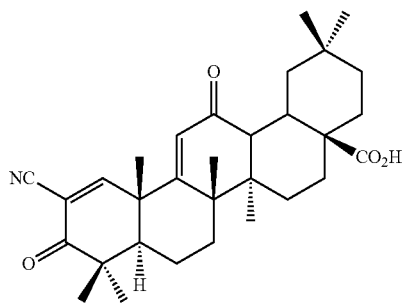

have been found to be effective in suppression of human breast cancer cell growth, and highly potent in many vitro assay systems such as: suppression of nitric oxide and prostaglandin production in macrophages, inhibition of growth of human breast cancer cells, suppression of nitric oxide formation in rat prostate cells, and suppression of prostaglandin formation in human colon fibroblasts, as detailed in the Figures.

These compounds have utility for prevention and treatment of cancer, Alzheimer's disease, Parkinson's disease, multiple sclerosis, amyotrophic lateral sclerosis, rheumatoid arthritis, inflammatory bowel disease, and all other diseases whose pathogenesis is believed to involve excessive production of either nitric oxide or prostaglandins.

The aberrant or excessive expression of either iNOS or COX-2 has been implicated in the pathogenesis of many disease processes, including carcinogenesis in the colon. Thus, overexpression of the gene for COX-2 is an early and central event in colon carcinogenesis (Prescott and White, 1996; Dubois et al., 1996). Mice with defects in the APC (adenomatous polyposis coli) gene develop large numbers of intestinal polyps at an early age, and marked elevations in COX-2 enzyme levels have been found in these polyps. These animal findings correlate with the finding of elevated levels of COX-2 mRNA and protein in many human primary colon cancers and colon cancer cell lines (Prescott and White, 1996), and it is believed that this elevation in COX-2 leads to a suppression of apoptosis, which would ordinarily lead to death of preneoplastic cells (Tsujii and DuBois, 1996). The functional relevance of COX-2 to intestinal tumorigenesis has been demonstrated by knockout of the COX-2 gene and the subsequent mating of mice bearing this knockout with polyp-forming mice bearing lesions in the APC gene; the COX-2 knockout caused a dramatic diminution in the number of polyps in the offspring (Oshima et al., 1996). Furthermore, treatment of experimental animals with either selective COX-2 inhibitors or non-selective COX-1/COX-2 inhibitors has been reported to be a potent approach to chemoprevention of intestinal cancer (Marnett, 1992; Oshima et al., 1996; Boolbol et al., 1996; Reddy et al., 1996; Sheng et al., 1997). As for the role of iNOS in carcinogenesis, it is clear that NO is a potent mutagen (Tamir and Tannebaum, 1996), and that nitric oxide can also activate COX-2 (Salvemini et al., 1993, 1994). Furthermore, there is a marked increase in iNOS in rate colon tumors induced by the carcinogen, azoxymethane (Takahashi et al., 1997).

MS is known to be an inflammatory condition of the central nervous system (Williams, Ulvestad and Hickey, 1994; Merrill and Beneviste, 1996; Genain and Nauser, 1997). Inflammatory, oxidative, or immune mechanisms may be involved in the pathogenesis of MS, AD, PD, and ALS (Bagasra et al., 1995; Griffin et al., 1995; McGeer and McGeer, 1995; Good et al., 1996; Simonian and Coyle, 1996; Kaltschrnidt et al., 1997). Both reactive astrocytes and activated microglia have been implicated in causation of NDD/NID; there has been a particular emphasis on microglia as cells that synthesize both NO and prostaglandins as products of the respective enzymes, iNOS and COX-2. De novo formation of these enzymes may be driven by inflammatory cytokines such as interferon-gamma or interleukin-1. In turn, excessive production of NO may lead to inflammatory cascades and/or oxidative damage in cells and tissues of many organs, including neurons and oligodendrocytes of the nervous system, with consequent manifestations in AD and MS, and possible PD and ALS (Coyle and Puttfarcken, 1993; Goodwin et al., 1995; Beal, 1996; Good et al., 1996; Merrill and Benvenist, 1996; Simonian and Coyle, 1996; Vodovotz et al., 1996). Epidemiologic data indicate that chronic use of NSAID's which block synthesis of prostaglandins from arachidonate, markedly lower the risk for development of AD (McGeer et al., 1996; Stewart et al., 1997). Thus, agents that block formation of NO and prostaglandins, may be used in approaches to prevention and treatment of NDD.

Further disclosed herein are the synthesis and biological activities of a new synthetic oleanane triterpenoid, CDDO, that has three important properties: 1) it is a potent agent for induction of differentiation in both malignant and non-malignant cells; 2) it is active at nanomolar levels as an inhibitor of proliferation of many malignant or premalignant cells; and 3) it is 100- to 500-fold more potent than any previous triterpenoid in suppressing the de novo synthesis of the inflammatory enzymes, iNOS and COX-2. These three actions are important for the development of a useful new chemopreventive agent, and they are also relevant to therapy of malignancy itself as well.

The practice of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, *Genetics; Molecular Cloning A Laboratory Manual*, 2nd Ed., ed. by Sambrook, J. et al. (Cold Spring Harbor Laboratory Press (1989)); *Short Protocols in Molecular Biology*, 3rd Ed., ed. by Ausubel, F. et al. (Wiley, NY (1995)); *DNA Cloning*, Volumes I and II (D. N. Glover ed., 1985); *Oligonucleotide Synthesis* (M. J. Gait ed. (1984)); Mullis et al. U.S. Pat. No. 4,683,195; *Nucleic Acid Hybridization* (B. D. Hames & S. J. Higgins eds. (1984)); the treatise, *Methods In Enzymology* (Academic Press, Inc., N.Y.); *Immunochemical Methods In Cell And Molecular Biology* (Mayer and Walker, eds., Academic Press, London (1987)); *Handbook Of Experimental Immunology*, Volumes I-IV (D. M. Weir and C. C. Blackwell, eds. (1986)); and Miller, J. *Experiments in Molecular Genetics* (Cold Spring Harbor Press, Cold Spring Harbor, N.Y. (1972)).

The invention is further illustrated by the following examples which should not be construed as further limiting the subject invention. The contents of all references, issued patents, and published patent applications cited throughout this application including the background are hereby incorporated by reference. A demonstration of efficacy of the therapeutic compounds of the present invention in the model(s) described in the Examples and Figures is predictive of efficacy in humans.

Example 1

Compounds were synthesized as below:

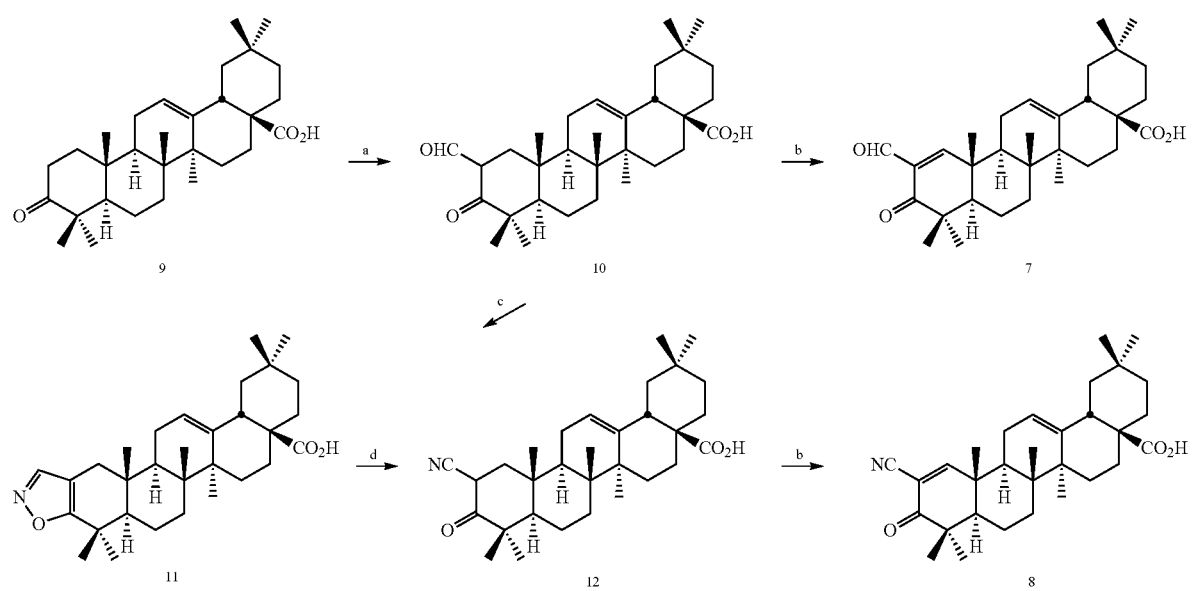

Scheme 1

Scheme 2

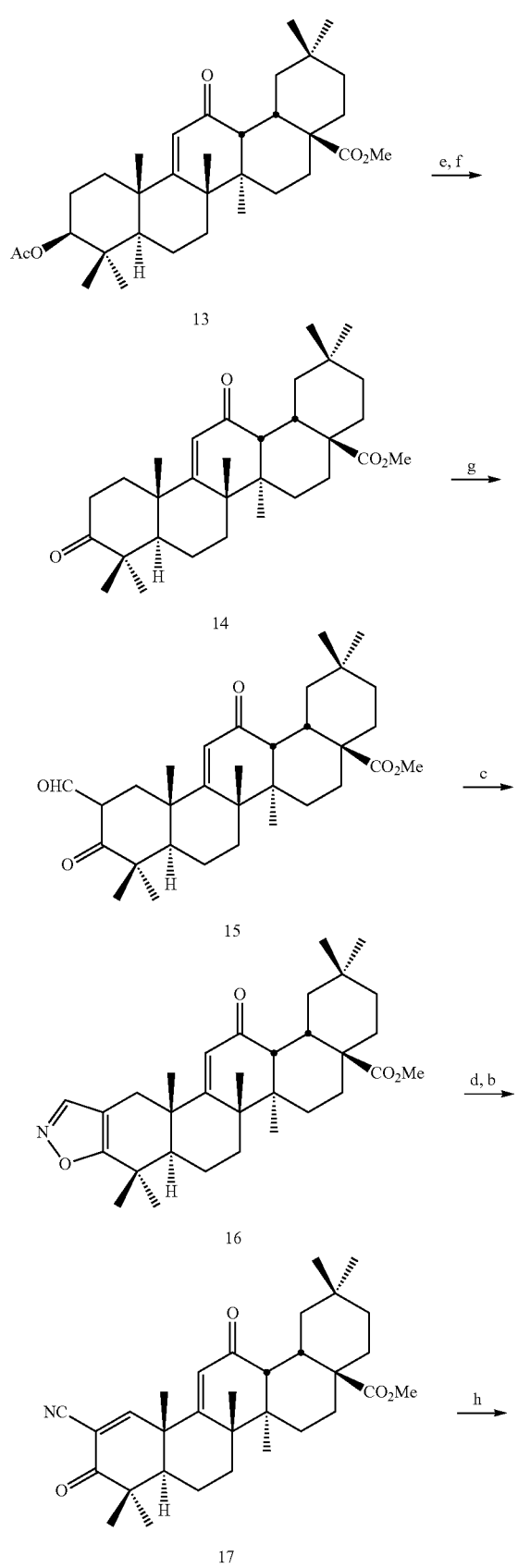

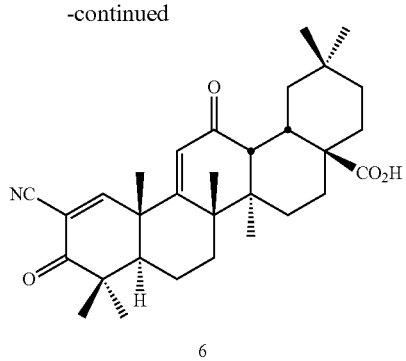

a: HCO₂Et/MeONa/THF,
b: PhSeCl/AcOEt; 30%H₂O₂/THF,
c: NH₂OH-HCl/EtOH/H₂O,
d: MeONa/MeOH/Et₂O,
e: KOH/MeOH,
f: Jones,
g: HCO₂Et/MeONa/PhH,
h: LiI/DMF.

Compound 10 was prepared by formylation of OA (Compound 9) (Simonsen and Ross, 1957) with ethyl formate in the presence of sodium methoxide in THF (Clinton et al., 1961). Compound 7 was obtained by introduction of a double bond at C-1 of Compound 10 with phenylselenenyl chloride in ethyl acetate and sequential addition of 30% hydrogen peroxide (Sharpless et al., 1973). Compound 11 was synthesized from Compound 10 by addition of hydroxylamine in aqueous ethanol; cleavage of Compound 11 with sodium methoxide gave Compound 12 (Johnson and Shelberg, 1945). Compound 14 was prepared from Compound 13 (Picard et al., 1939) by alkali hydrolysis followed by Jones oxidation. Compound 15 was prepared by formylation of Compound 14 with ethyl formate in the presence of sodium methoxide in benzene. Compound 16 was synthesized from Compound 15 by addition of hydroxylamine. Nitrile 17 was obtained by cleavage of isoxazole 16 with sodium methoxide (yield, 100%), followed by introduction of a double bond at C-1 with PhSeCl—H₂O₂ (yield, 40%). CDDO (6) was prepared in 71% yield by halogenolysis of 17 with lithium iodide in DMF (Dean, P. D. G., 1965).

The inhibitory activities of these compounds and dexamethasone on IFN-γ induced NO production in mouse macrophages is shown below in Table 1. The following procedure for the assay was used. Macrophages were harvested from female mice injected intraperitoneally four days previously with 4% thioglycollate. These cells were seeded in 96-well tissue culture plates and incubated with 4 ng/mL IFN-γ in the presence or absence of inhibitory test compounds. After 48 hours NO production (measured as nitrite by the Griess reaction) was determined. Full details of the assay are given in Ding et al., 1990; Bogdan et al., 1992. Compound 6 (CDDO) showed excellent inhibitory activity (IC₅₀, 1 nM) similar to that of dexamethasone.

TABLE 1

IC$_{50}$ (μM)$^a$ Values for Inhibition of IFN-γ-Induced NO Production in Mouse Macrophages.

| Compound | IC$_{50}$ (μM) |
| --- | --- |
| dexamethasone | 0.001 |
| 1 | 0.6 |
| 2 | 0.9 |
| 3 | 6 |

TABLE 1-continued

IC$_{50}$ (μM)[a] Values for Inhibition of IFN-γ-Induced
NO Production in Mouse Macrophages.

| Compound | IC$_{50}$ (μM) |
|---|---|
| 4 | 30 |
| 5 | 27 |
| 6 | 0.001 |
| 7 | >1.0[b] |
| 8 | .9 |

[a]IC50 (μM) values of compounds 1-5, 7 and 8 were determined in the range of 0.01-40 μM (4-fold dilutions) and the ones of dexamethasone and 6 were determined in the range of 1 μM-0.1 pM (10 fold dilutions). Values are the average of two separate experiments.
[b]Compound 7 was very toxic above 1 μM and not active below 1 μM.

All new compounds 6-8 exhibited satisfactory spectral data including high-resolution mass spectra and elemental analysis.

For the following examples, stock solutions of CDDO (0.01 M) were made in DMSO and aliquots frozen at −20° C. Serial dilutions were made in DMSO before addition to cell culture media. Primary rat microglia and hippocampal neurons were isolated and cultured as described by Flaris et al., 1993 and Ren and Flanders, 1996.

Example 2

Figure 11B:
FIGS. 11(A)-(H) shows induction of differentiation by CDDO in LCDB leukemia cells (A-D), PC12 cells (E-H)
Figure 11D:
Figure 11A:
Figure 11C:
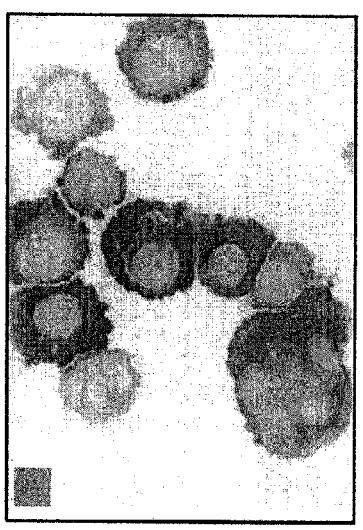
Figure 11F:
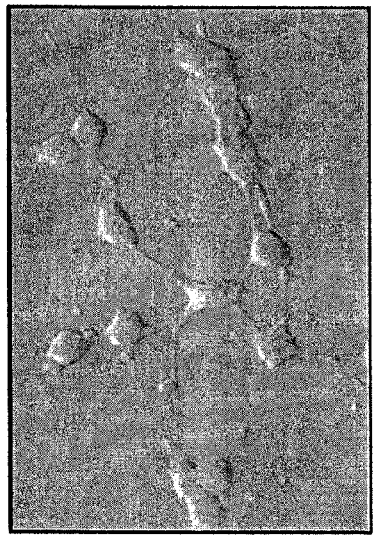
Figure 11H:
Figure 11E:
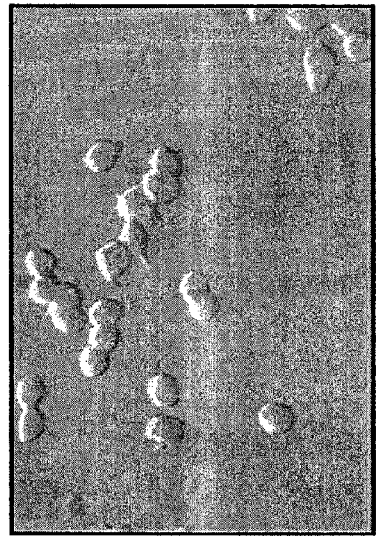
Figure 11G:
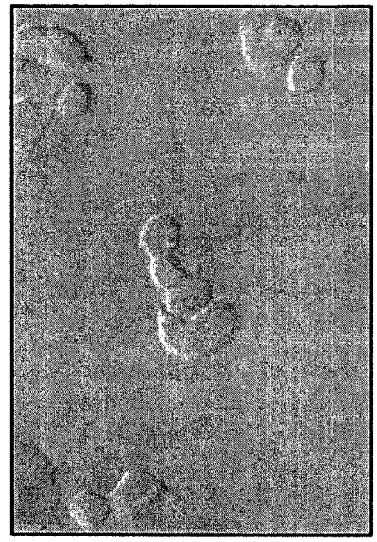
Figure 12A:
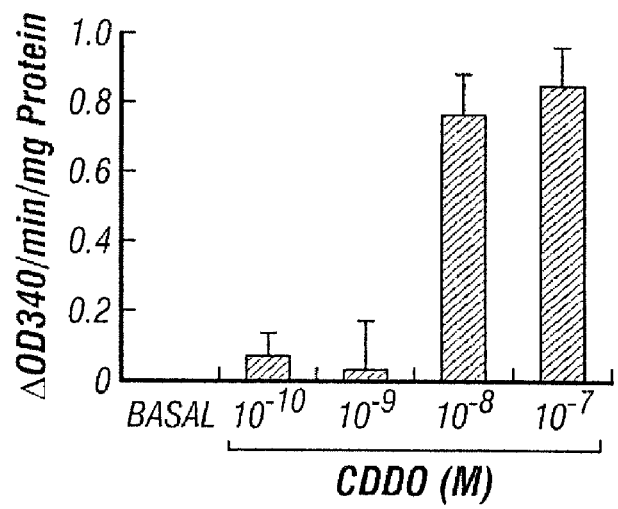
FIGS. 12 (A)-(B) shows induction of differentiation by CDDO in 3T3-L1 fibroblasts.
Figure 12B:
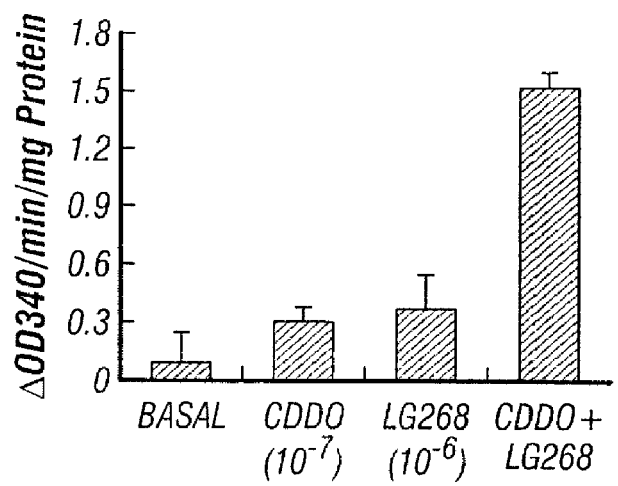

Induction of Differentiation in Myelogenous Leukemia Cells, PC12 Pheochromocytoma Cells, and 3T3-L1 Fibroblasts CDDO induces monocytic differentiation in the poorly differentiated LCDB acute myelogenous leukemia cell line, derived from a chemotherapy-resistant patient at the NCI Pediatric Oncology Branch. FIG. 11 illustrates LCDB cells seeded in RPMI 1640/2% FBS, either alone (11A), with 2.5 ng/ml TGF-β1 (11B), with 10$^{-8}$M CDDO (11C), or with both TGF-β1 and CDDO (11D). After 48 h, cytospin slide preparations were made and stained for α-naphthyl acetate esterase activity (kit from Sigma). PC12 cells were cultured for 5 days in gridded dishes in DMEM/10% FBS and 5% horse serum (Smith et al., 1997), either alone (11E), with 100 ng/ml 7S NGF (11F), with 10$^{-6}$ M CDDO (11G), or with both NGF and CDDO (11H). Cells were plated in triplicate, and for each treatment similar results were observed in at least two separate platings of cells. Methods for quantitative image analysis of size of cells and neurites have been described (De la Torre et al., 1997). Control cells in FIG. 11E are approximately 10 μm in diameter. 3T3-L1 cells were grown to confluency in DMEM/5% calf serum, and then treated once with CDDO in DMEM/10% FBS (FIG. 12A) or with CDDO and/or LG100268 in DMEM/10% FBS (FIG. 12B). Every two days thereafter, medium was changed to DMEM/10% FBS, without added CDD0 or LG100268., Cells were harvested on day 8 (FIG. 12A) or day 6 (FIG. 12B), and GPDH was measured in lysates, using a standard assay for consumption of NADH at 340 nm (Wise and Green, 1979). These cells do not express the monocyte/macrophage marker, α-naphthyl esterase (FIG. 11A). However, within 48 h, CDDO (10$^{-8}$ M) induced the activity of this enzyme, as determined histochemically (FIG. 11C). Treatment of LCDB cells with TGF-131 (2.5 ng/ml) also induced α-naphthyl esterase activity (FIG. 11B), and there was an additive effect when both agents are used (FIG. 11D). It has been shown that CDDO has differentiative effects, either by itself or in combination with TGF-β1, on the human monocytic leukemia line, THP-1, and the human promyelocytic leukemia line, NB4 (data not shown).

The rat pheochromocytoma cell line, PC12, has been widely used to study neuronal development and differentiation. Treatment of these tumor cells with NGF is known to induce a neuronal phenotype, with extensive neurite outgrowth (Greene and Rischler, 1976; Guroff 1985). CDDO markedly potentiates these effects of NGF. FIGS. 11E and F show the induction of neurite outgrowth by NGF (100 ng/ml). Although CDDO (10$^{-6}$ M) by itself does not induce neurite formation, it does cause the cells to adopt a larger, flatter morphology (FIG. 11G). When used in combination with NGF, CDDO (FIG. 11H) almost doubled the number of primary neurites/cell (from 1.2±0.2 S.E.M. to 2.1±0.1, p<0.001), and caused a greater than 3-fold increase in length of neurites (from 28±6 to 99±9 microns, p<0.001), and a 5-fold increase in neurite branching/cell (from 0.23±0.06 to 1.13±0.08, p<0.001). Thus, CDDO enhances neuronal differentiation of PC12 cells by increasing cell size, as well as the extent and complexity of neurite arborization.

A third cell type in which CDDO induces differentiation is the 3T3-L1 fibroblast. These non-neoplastic fibroblasts are classically induced to form adipocytes by the combination of insulin, dexamethasone, and IBMX (Green and Kehinde, 1974; Bernlohr et al., 1984). Treatment with CDDO (FIG. 12A) at doses as low as 10$^{-8}$ M (in the absence of added insulin, dexamethasone, and IBMX) caused adipogenic differentiation, as measured by induction of the marker, GPDH (Wise and Green, 1979), known to be a key enzyme in triglyceride synthesis. The results with the enzyme assay have been confirmed by oil red 0 staining for fat droplets (data not shown). Furthermore, CDDO acts synergistically with the RXR-selective retinoid, LG100268 (Boehm et al., 1995) to promote adipogenic differentiation (FIG. 12B).

Example 3

CDDO Inhibits Proliferation of Many Malignant or Premalignant Cells

Figure 13A:
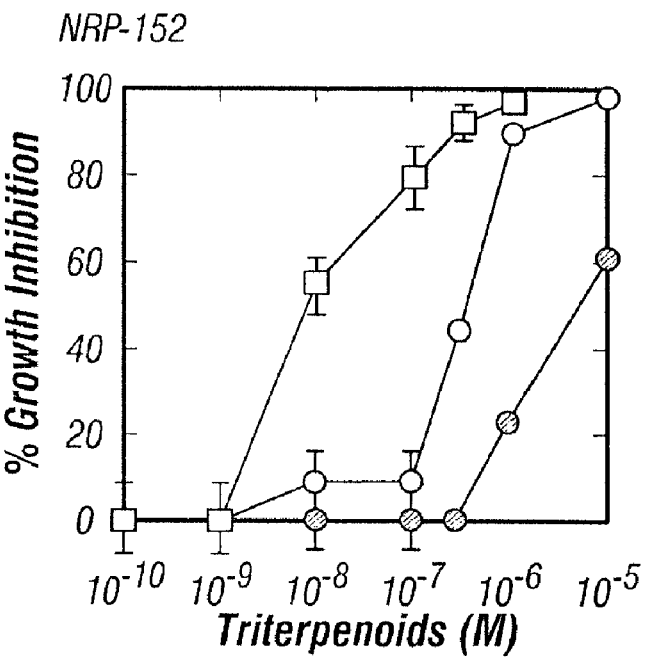
FIGS. 13(A)-(B) illustrates dose-response curves for suppression of cell growth in NRP-152 and MCF-7 cells by CDDO (■), TP-82 (○), and oleanolic acid (●).
Figure 13B:
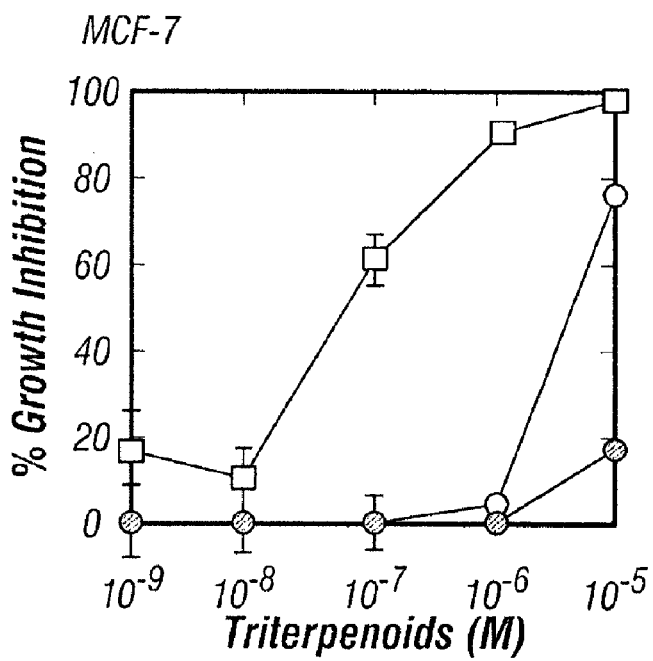

Inhibitors of cell proliferation are known to be useful chemopreventive and chemotherapeutic agents. CDDO was tested against a wide variety of cells derived from highly aggressive leukemias and carcinomas, as well as from non-neoplastic tissues. NRP-152 cells were grown as described in Danielpour et al., 1994. MCF-7 cells were grown in phenol red-free RPMI 1640/10% charcoal-stripped FBS with added 17-β-estradiol (10 μM). Triterpenoids were added at the time of plating, and 72 h later $^3$H-thymidine (1 μCi/well) was added for the final 2 h of incubation. Incorporation of thymidine was measured after cells were precipitated with TCA (10%), washed, and solubilized. The symbols used in FIGS. 13(A)-(B) are CDDO, ■; TP-82, ○, and oleanolic acid; ●.

Typical dose-response curves are shown in FIGS. 13(A)-(B) for two cell types, human MCF-7 breast carcinoma and rat NRP-152 non-malignant prostate epithelium (Danielpour et al., 1994). CDDO is highly active in the nanomolar range in suppressing thymidine incorporation in these cells, while TP-82 is markedly less active, and oleanolic acid, is virtually without activity at concentrations of 1 μM or less.

Results obtained with other cancer cells are shown in Table 2. Note that: (1) several lines of estrogen receptor-negative breast cancer cells are sensitive to CDDO, as well as estrogen receptor-positive MCF-7 cells; (2) even if tumor cells have a Smad-4/DPC4 mutation and are therefore insensitive to the growth-inhibitory actions of TGF-β (Schutte et al., 1996; Zhou et al., 1998; Heldin et al., 1997), they still may respond to CDDO, as can be seen in the case of SW626 ovarian carcinoma, CAPAN-1 and AsPc-1 pancreatic carcinoma, and MDA-MB-468 breast carcinoma cells; (3) many leukemia cells, especially of the myeloid lineage, are highly sensitive to CDDO.

TABLE 2

Inhibition of cell proliferation by CDDO

| Cell | Cell type | IC$_{50}$ (M) |
|---|---|---|
| MCF-7 | ER positive breast carcinoma | $3 \times 10^{-8}$ |
| MDA-MB-231 | ER negative breast carcinoma | $1 \times 10^{-6}$ |
| 21-MT-1 | ER negative breast carcinoma | $2 \times 10^{-7}$ |
| 21-MT-2 | ER negative breast carcinoma | $3 \times 10^{-7}$ |
| 21-NT | ER negative breast carcinoma | $1 \times 10^{-6}$ |
| 21-PT | ER negative breast carcinoma | $3 \times 10^{-7}$ |
| THP-1 | Monocytic leukemia | $5 \times 10^{-8}$ |
| U937 | Monocytic leukemia | $2 \times 10^{-7}$ |
| HL-60 | Myelocytic leukemia | $1 \times 10^{-7}$ |
| NB4 | Promyelocytic leukemia | $4 \times 10^{-8}$ |
| AML193 | Acute myelocytic leukemia | $4 \times 10^{-7}$ |
| KG-1 | Acute myeloid leukemia | $2 \times 10^{-7}$ |
| ML-1 | Myeloblastic leukemia | $1 \times 10^{-7}$ |
| NT2/D1 | Embryonal carcinoma | $1 \times 10^{-7}$ |
| A2058 | Melanoma | $2 \times 10^{-7}$ |
| MDA-MB-468[a] | ER negative breast carcinoma | $2 \times 10^{-7}$ |
| SW626[a] | Ovarian carcinoma | $3 \times 10^{-7}$ |
| AsPc-1[a] | Pancreatic carcinoma | $1 \times 10^{-7}$ |
| CAPAN-1[a] | Pancreatic carcinoma | $3 \times 10^{-7}$ |

All cells were obtained from ATCC, except as noted. They were grown under standard conditions in either DMEM, DMEM/F12, or RPMI 1640 media plus 5-10% FBS. CDDO, over the dose range $10^{-6}$ to $10^{-10}$M, was added to cultures at the time of seeding. Three or 4 days later, cells were treated with ³H-thymidine for 2 h (12 h in the case of leukemia cells), and then incorporation was measured. "ER" means estrogen receptor.
[a]These cells all have Smad4/DPC4 mutations (Schulte et al. 1996).

Example 4

CDDO Blocks De Novo Synthesis of iNOS and COX-2

CDDO is highly active in blocking the ability of several inflammatory cytokines to induce de novo formation of the enzymes, iNOS and COX-2 (FIG. 14). FIG. 14(A) illustrates Western blots; primary mouse macrophages; IFN-γ, 10 ng/ml; LPS, 2 ng/ml were added to cultures together with triterpenoids or dexamethasone (concentrations shown as μM); cells were harvested at 12 h. FIG. 14(B) illustrates Northern blots, RAW 264.7 macrophage-like cell line. IFN-γ, 10 ng/ml; LPS, 1 ng/ml; TNF-α, 10 ng/ml, were added to cultures together with CDDO or dexamethasone. RNA prepared after 12 h; GAPDH used as a loading control. FIG. 14(C) illustrates suppression of production of NO and PGE$_2$ in primary macrophages. For NO studies, cells were treated with IFN-γ, 10 ng/ml, together with CDDO (■), dexamethasone (○), TP-82 (□), or oleanolic acid (▲). After 48 h, supernatants were analyzed for NO by the Griess reaction. For PGE$_2$ studies, cells were treated with IFN-γ, 5 ng/ml, and LPS, 5 ng/ml, together with the same set of inhibitors. After 48 h, PGE$_2$ was measured in supernatants by immunoassay. Control values (no inhibition) for NO and PGE$_2$ were 4.7 nmol/2×10⁵ cells and 2.2 ng/ml/2×10⁵ cells, respectively. FIGS. (14D) and (14E) illustrate (human colon myofibroblasts) ¹⁸Co cells grown in MEM/10% FBS; other methods are the same as reported above for macrophages. FIG. 14(D) illustrates Northern blots showing dose-response for suppression of COX-2 mRNA after induction with IL-1β (30 pg/ml). CDDO was added together with IL-1. In FIG. (E), Western blots show suppression of COX-2 protein; CDDO was added together with IL-1β (30 pg/ml). Also shown is suppression of cumulative production of PGE$_2$ in cell supernatants by CDDO.

Figure 14A:
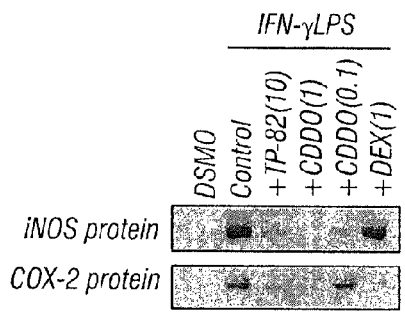
FIGS. 14 (A)-(E) shows inhibitory effects of triterpenoids on induction of iNOS and COX-2 in mouse macrophages and human colon fibroblasts.
Figure 14B:
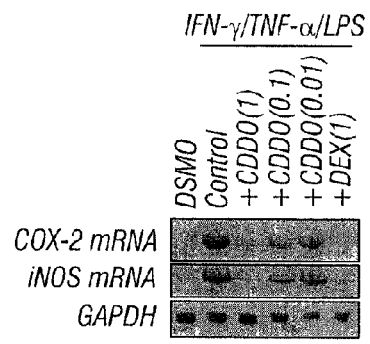
Figure 14C:
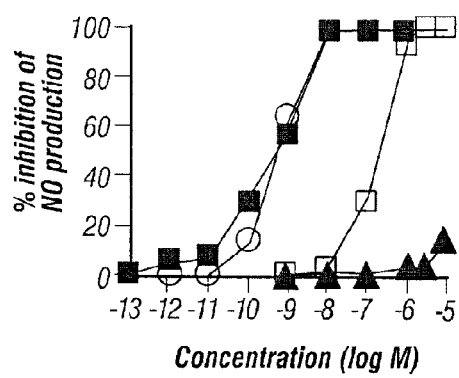
Figure 14D:
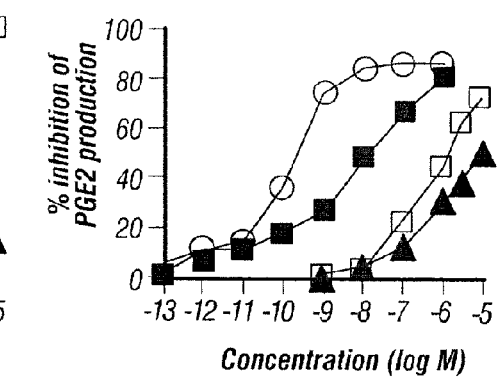
Figure 14D:
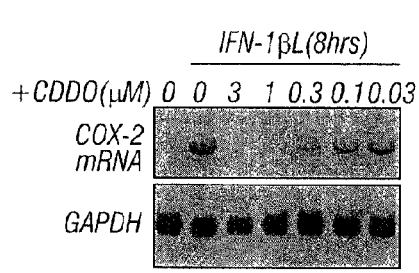
Figure 14E:
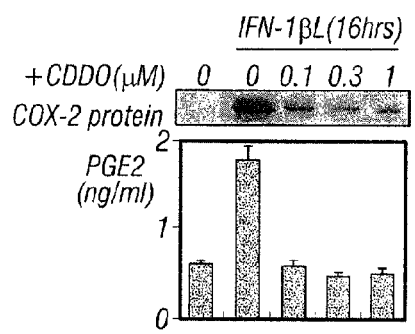

These effects of CDDO have been seen in primary mouse macrophages, a mouse macrophage-like tumor cell line (RAW 264.7), and in non-neoplastic human colon fibroblasts. FIG. 14A shows Western blots for expression of iNOS and COX-2 protein in primary macrophages. Neither iNOS nor COX-2 expression can be detected in these cells until they are stimulated by an inflammatory mediator such as IFN-γ or LPS. CDDO at concentrations of 1 μM or less blocked expression of both iNOS and COX-2 protein. The importance of the nitrile function at C-2 of CDDO, as seen above in FIG. 13, is again shown in FIG. 14A. FIG. 14B shows Northern blots indicating that CDDO ($10^{-6}$ M) lowered levels of mRNA expression for both iNOS and COX-2 in RAW 264.7 cells by greater than 75%. The above effects on iNOS and COX-2 are also reflected in the cumulative production of their respective enzyme products, NO and PGE$_2$, as measured in primary macrophages (FIG. 14C). Significant inhibition by CDDO was found at levels as low as $10^{-9}$ M, and again it was markedly more active than TP-82 or oleanolic acid. However, CDDO is not a direct inhibitor of the enzymatic activity of either iNOS or COX-2, since it has no immediate effect on NO or prostaglandin production if it is added to RAW cells in which synthesis of these two enzymes has already been induced (data not shown). Likewise, the actions of CDDO are not blocked by the glucocorticoid antagonist, RU-486, which is known to bind to the glucocorticoid receptor (data not shown). In these regards, CDDO is identical to the other oleanolic acid derivatives previously studied (Suh et al., 1998).

A second type of cell in which CDDO is a highly effective inhibitor of the de novo formation of COX-2 is the colon myofibroblast. These cells were selected because of the importance of stromal cell COX-2 in colon carcinogenesis (Oshima et al., 1996). CDDO blocked induction of COX-2 mRNA and protein caused by treatment of non-neoplastic ¹⁸Co cells with IL-1 (FIGS. 14D, E); again, this action was reflected in a lowering of PGE$_2$ levels in the culture medium. Although CDDO effectively blocks the induction of COX-2 by agents such as IFN-γ, LPS, TNF-α, and IL-1, CDDO is ineffective when TPA is used as the inducer of COX-2. This has been seen in 18Co cells, as well as in the human mammary epithelial cell line, 184B5/HER (Zhai et al., 1993).

Example 5

CDDO Suppresses iNOS and Protects Against Cell Death in Rat Brain Cells

The roles of inflammatory mediators, as well as aberrant programs for cell survival and apoptosis, in the genesis of cancer and Alzheimer's Disease are now undergoing serious investigation (McGeer and McGeer, 1995; Merrill and Benveniste, 1996; Akama et al., 1998). CDDO was tested in this example as a suppressor of de novo formation of iNOS in cultured microglia (the resident macrophages of the brain), as well as its ability to protect cultured hippocampal neurons from cell death induced by β-amyloid. It was found that CDDO acts in primary microglial cultures in a manner similar to that reported above for primary peritoneal macrophages. Thus, LPS (5 ng/ml) induced iNOS in primary microglial cultures and caused a 27-fold increase in production of NO within 18 h. Concomitant treatment of these cultures with CDDO at either $10^{-6}$ or $10^{-7}$ M inhibited this induction by 73% and 52%, respectively. We have also explored the possibility that CDDO can protect cultured hippocampal neurons from cell death induced by the peptide β-amyloid, since NO has been implicated (Akama et al., 1998) in the neurotoxic actions of this peptide which is central to the pathogenesis of Alzheimer's disease (Selkoe, 1997). Hippocampal neurons were isolated and cultured from 16 day rat embryos and then treated with CDDO for 24 h' before adding the β-amyloid peptide fragment, amino acids 25-35, at a final concentration of 10 μM. This dosing with β-amyloid alone caused death of more than half of the neurons in the culture within 24 h, as measured by MTT assay. However, pretreatment of the neuronal cultures with CDDO ($10^{-8}$ and $10^{-7}$ M) totally prevented this cell death, and some protective activity of CDDO was found at doses as low as $10^{-10}$ M.

SUMMARY

As seen above, compounds of the invention such as CDDO are potent, multifunctional molecules having a wide range of actions, many of them potentially useful for prevention or treatment of diseases such as cancer. Proliferation of many human tumor cell lines, including those derived from estrogen receptor-positive and -negative breast carcinomas, myeloid leukemias, and several carcinomas that bear a Smad-4 mutation are inhibited. The ability of various inflammatory cytokines, such as interferon-γ, interleukin-1, or tumor necrosis factor-α to induce de novo formation of the enzymes, inducible nitric oxide synthase (iNOS) or inducible cyclooxygenase (COX-2) in either mouse peritoneal macrophages, rat brain microglia, or human colon fibroblasts is suppressed. Also, brain hippocampal neurons are protected from cell death induced by β-amyloid. The above indicates that the compounds of the invention, e.g., CDDO, are useful in vivo, either for chemoprevention or chemotherapy of malignancy, as well as for neuroprotection.

EQUIVALENTS

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

What is claimed is:
1. A compound of the formula:

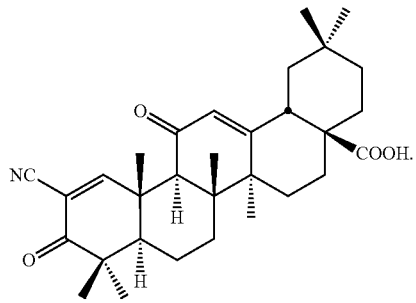

* * * * *

UNITED STATES PATENT AND TRADEMARK OFFICE
CERTIFICATE OF CORRECTION

PATENT NO. : 8,586,775 B2
APPLICATION NO. : 13/217127
DATED : November 19, 2013
INVENTOR(S) : Gordon W. Gribble et al.

It is certified that error appears in the above-identified patent and that said Letters Patent is hereby corrected as shown below:

In item 56 on the title page, Other Publications, please delete the 3rd reference: "Baeuerle, "The NF-κB: ten years after," *Cell*, 87:13-20, 1996." and replace with -- Baeuerle, "NF-κB: ten years after," *Cell*, 87:13-20, 1996. --

In item 56 on title page 2, Other Publications, please delete the 16th reference in the left column:

"Chung and Wasicak, "Synthesis of chiral ∀-acetylenic cyclic amines from ∀-amino acids: App.s to differentially constrained oxotremorine analogues as muscarinic agents," *Tetrahedron Lett.*, 31:3957-3960, 1990." and replace with -- Chung and Wasicak, "Synthesis of chiral α-acetylenic cyclic amines from α-amino acids: Applications to differentially constrained oxotremorine analogues as muscarinic agents," *Tetrahedron Lett.*, 31:3957-3960, 1990. --

In item 56 on title page 2, Other Publications, please delete the 8th reference in the right column: "Elstner, et al., "Ligands for peroxisome proliferation-activated receptorgamma and retinoic acid receptor inhibit growth and induce apoptosis of human breast cancer cells in vitro and in BNX mice," *Proc. Natl. Acad. Sci., USA*, 95:8806-8811, 1998." and replace with -- Elstner, et al., "Ligands for peroxisome proliferation-activated receptor gamma and retinoic acid receptor inhibit growth and induce apoptosis of human breast cancer cells in vitro and in BNX mice," *Proc. Natl. Acad. Sci., USA*, 95:8806-8811, 1998. --

In item 56 on title page 2, Other Publications, please delete the 19th reference in the right column: "García-Granados, et al., "Semi-synthesis of triterpene A-ring derivatives from oleanolic and maslinic acids. Part II. Theoretical and experimental $^{13}$C chemical shifts," *J. of Chemical Research*, Synopses, 2:56-57, 2000." and replace with -- García-Granados, et al., "Semi-synthesis of triterpene A-ring derivatives from oleanolic and maslinic acids. Theoretical and experimental $^{13}$C chemical shifts," *J. of Chemical Research*, Synopses, 2:56-57, 2000. --

In item 56 on title page 2, Other Publications, please delete the 23rd reference in the right column: "Glen, et al., "Isolation of a new triterpenoid from rose bay willow-herb," *Chemistry and Industry*, London, United Kingdom), 46:1908, 1965." and replace with -- Glen, et al., "Isolation of a new Signed and Sealed this
Twenty-fifth Day of February, 2014

Michelle K. Lee
*Deputy Director of the United States Patent and Trademark Office*

CERTIFICATE OF CORRECTION (continued)

triterpenoid from rose bay willow-herb," *Chemistry and Industry*, (London, United Kingdom), 46:1908, 1965. --

In item 56 on title page 4, Other Publications, please delete the 10th reference in the left column: "Lehn and Ourisson, "Nuclear magnetic resonance (N.M.R.) of natural products. I. General introduction. Triterpenes of the lupane series. Methyl groups," *Bulletin de la Societe Chimique de France*, 1137-1142, 1962. (French only, but see attached English Caplus database summary.)." and replace with -- Lehn and Ourisson, "Nuclear magnetic resonance (N.M.R.) of natural products. I. General introduction. Triterpenes of the lupane series. Methyl groups," *Bulletin de la Societe Chimique de France*, 1137-1142, 1962. (French only, but see attached English CAPLUS database summary.). --

In item 56 on title page 4, Other Publications, please delete the 20th reference in the left column: "Manzoor-i-Khuda and Habermehl, "Chemical constituents of *Corchorus capsularis*and *C. olitorium* (jute plant). III. Structure of corosin," *Zeitschrift fuer Naturforschung, Teil C: Biochemie, Biophysik, Biologie, Virologie,*29 (5-6): 209-221, 1974." and replace with -- Manzoor-i-Khuda and Habermehl, "Chemical constituents of *Corchorus capsularis* and *C. olitorium* (jute plant). III. Structure of corosin," *Zeitschrift fuer Naturforschung, Teil C: Biochemie, Biophysik, Biologie, Virologie,* 29(5-6):209-221, 1974. --

In item 56 on title page 5, Other Publications, please delete the 25th reference in the right column: "Ruvolo, et al., "The novel triterpenoid methyl CDDo inhibits Bcl2 phosphorylation and potently kolls U937 cells," *Blood*, 94(10), Suppl. 1, Part 1: 280A, abstract #1251, 1999." and replace with -- Ruvolo, et al., "The novel triterpenoid methyl CDDO inhibits Bcl2 phosphorylation and potently kills U937 cells," *Blood*, 94(10), Suppl. 1, Part 1: 280A, abstract #1251, 1999. --

In item 56 on title page 6, Other Publications, please delete the first reference in the left column: "Sheng, et al., "A selective cyclooxygenase 2 inhibitor suppresses the growth of H-ras-transformed rat intestinal epithelial cells," *Gastroenterology*, 113(6):1883-18891, 1997." and replace with -- Sheng, et al., "A selective cyclooxygenase 2 inhibitor suppresses the growth of H-ras-transformed rat intestinal epithelial cells," *Gastroenterology*, 113(6):1883-1891, 1997. --

In item 56 on title page 6, Other Publications, please delete the 22nd reference in the right column: "Warrell, et al., "Differentiation therapy of acute promyelocytic leukemia with tretinoin (alltrans-retinoic acid)," *N. Engl. J. Med.*, 324(20):1385-1393, 1991." and replace with -- Warrell, et al., "Differentiation therapy of acute promyelocytic leukemia with tretinoin (all-trans-retinoic acid)," *N. Engl. J. Med.*, 324(20):1385-1393, 1991. --